US007687500B2

(12) United States Patent
Howell et al.

(10) Patent No.: US 7,687,500 B2
(45) Date of Patent: Mar. 30, 2010

(54) SUBSTITUTED OXETANES, METHOD OF MAKING, AND METHOD OF USE THEREOF

(75) Inventors: Amy R. Howell, Tolland, CT (US); Rosa C. Taboada, Hamden, CT (US); Stewart K. Richardson, Tolland, CT (US)

(73) Assignee: The University of Connecticut, Storrs, CT (US)

( * ) Notice: Subject to any disclaimer, the term of this patent is extended or adjusted under 35 U.S.C. 154(b) by 233 days.

(21) Appl. No.: 12/019,010

(22) Filed: Jan. 24, 2008

(65) Prior Publication Data

US 2008/0139566 A1 Jun. 12, 2008

Related U.S. Application Data

(62) Division of application No. 10/992,805, filed on Nov. 19, 2004, now Pat. No. 7,351,827.

(51) Int. Cl.
| | |
|---|---|
| A61K 31/53 | (2006.01) |
| A61K 31/506 | (2006.01) |
| A61K 31/4412 | (2006.01) |
| A61K 31/4427 | (2006.01) |
| C07D 253/02 | (2006.01) |
| C07D 239/36 | (2006.01) |
| C07D 239/47 | (2006.01) |
| C07D 239/545 | (2006.01) |
| C07D 239/553 | (2006.01) |
| C07D 239/557 | (2006.01) |
| C07D 239/56 | (2006.01) |
| C07D 239/58 | (2006.01) |
| C07D 213/61 | (2006.01) |
| C07D 213/64 | (2006.01) |
| C07D 213/69 | (2006.01) |
| C07D 213/70 | (2006.01) |
| C07D 213/73 | (2006.01) |
| C07D 213/78 | (2006.01) |

(52) U.S. Cl. .................. 514/242; 514/245; 514/274; 514/336; 514/348; 514/349; 544/182; 544/209; 544/212; 544/311; 544/314; 544/316; 544/317; 544/318; 546/296

(58) Field of Classification Search .................. None
See application file for complete search history.

(56) References Cited

U.S. PATENT DOCUMENTS

| | | | |
|---|---|---|---|
| 3,418,330 A | 12/1968 | Arnold et al. | |
| 3,498,896 A | 3/1970 | Arnold et al. | |
| 3,506,766 A | 4/1970 | Arnold et al. | |
| 3,616,377 A | 10/1971 | Arnold et al. | |
| 5,041,447 A | 8/1991 | Saito et al. | |
| 5,420,276 A | 5/1995 | Norbeck | |
| 6,001,841 A | 12/1999 | Cook et al. | |

FOREIGN PATENT DOCUMENTS

| | | |
|---|---|---|
| EP | 0 291 917 A2 | 11/1988 |
| EP | 0334250 | 9/1989 |
| EP | 0 416 605 A1 | 3/1991 |
| EP | 0 492 430 A1 | 7/1992 |
| EP | 0 493 722 A1 | 7/1992 |
| EP | 0 614 906 A1 | 9/1994 |
| FR | 1495279 | 9/1967 |

OTHER PUBLICATIONS

Structure described orally to Wesleyan University Audience, Jul. 2002, 1 pg.
NSF Grant No. 0111522 Abstract;www.fastlane.nsf.gov/servlet/showaward?award=0111522&fmt=text; published Aug. 15, 2001, 1 pg.
Howell Research Group; "Dichotomy of Reactivity of 1,5-Dioxaspiro[3.2]hexanes"; www.sp.uconn.edu/howell/Htm/dichotomy(overvw2).htm; Feb. 24, 2003.
Adam, Waldemar, et al; "A Convenient Preparation of Acetone Solutions of Dimethyldioxirane"; Chem. Ber.;1991;124 ;p. 2377.
Bookser, Brett C., et al; AMP Deaminase Inhibitors. 2. Initial Dicovery of a Non-Nucleotide Transition-State Inhibitor Series; J. Med. Chem.; 2000; 43; pp. 1495-1507.
Bookser, Brett C., et al; AMP Deaminase Inhibitors. 4. Further N3-Substituted Coformycin Aglycon Analogues: N3-Alkylmalonates as Ribose 5'-Monophosphate Mimetics; J. Med. Chem.;2000;43;pp. 1519-1524.
Ferrer, Marta, et al; "Easy Availability of More Concentrated and Versatile Dimethyldioxirane Solutions"; Tetrahedron Letters;vol. 37.; No. 20; pp. 3585-3586; 1996.
Ichikawa, Satoshi, et al; The First Synthesis of Herbicidin B. Stereoselective Construction of the Tricyclic Undecose Moiety by a Conformational Restriction Strategy Using Steric Repulsion between Adjacent Bulky Silyl Protecting Groups on a Pyranose Ring; J. Am. Chem. Soc.; 1999; 121; pp. 10270-10280.
Jacobson, Kenneth A, et al; "Methanocarba Analogues of Purine Nucleosides as Potent and Selective Adenosine Receptor Agonists"; J. Med. Chem.; 2000; 43; pp. 2196-2203.
Kasibhatla, Srinivas Rao, et al; "AMP Deaminase Inhibitors. 3. SAR of 3-(Carboxyarylalkyl)coformycin Aglycon Analogues"; J. Med. Chem.;2000; 43; pp. 1508-1518.
Kato, Keisuke, et al; "Total Synthesis of Uracil Polyoxin C"; Synthesis;1998; pp. 1527-1533.
Mulzer, Johann, et al; "A Deprotonation of B-Lactones—an Example of a "Forbidden" B Elimination"; J. Am. Chem. Soc.; 1980; 102; pp. 3620-3622.
Murray, R. W.; et al.;"Synthesis of Epoxides Using Dimethyldioxirane: trans-Stilbene Oxide"; Org. Syn.; 1996; 74; pp. 91-100.

(Continued)

*Primary Examiner*—Shaojia Anna Jiang
*Assistant Examiner*—Eric S Olson
(74) *Attorney, Agent, or Firm*—Cantor Colburn LLP

(57) ABSTRACT

Oxetane-containing nucleosides, particularly non-reducing psiconucleoside oxetanes are described herein. Therapeutic application of these oxetane compounds toward the treatment of nucleoside analog related disorders such as disorders involving cellular proliferation and infection are also described.

12 Claims, No Drawings

OTHER PUBLICATIONS

Nelson, Scott G., et al; Catalyzed acyl halide—aldehyde cyclocondensations. New insights into the design of catalytic cross aldol reactions; Tetrahedron Letters;40;(1999); pp. 6535-6539.

Taboada, Rosa, et al; "Directed Ring-Opening of 1,5-Dioxaspiro[3.2]hexanes: Selective Formation of 2,2-Disubstituted Oxetanes";Journal of Organic Chemistry; 2003; 68; pp. 1480-1488.

Terasaka, Tadashi, et al; "A Highly Potent Non-Nucleoside Adenosine Deaminase Inhibitor: Efficient Drug Discovery by Intentional Lead Hybridization"; J. Am. Chem. Soc.; 2004; 126; pp. 34-35.

Ugarkar, Bheemarao, G. et al; "Adenosine Kinase Inhibitors. 1. Synthesis, Enzyme Inhibition, and Antiseizure Activity of 5-Iodotubercidin Analogues"; J. Med. Chem.; 2000; 43; pp. 2883-2893.

International Search Report; International Application No. PCT/US2004/038989; International Filing Date Nov. 19, 2004; Applicant's File Reference: UCT-0050-PCT; Date of Mailing Apr. 18, 2005; 5 pages.

SUBSTITUTED OXETANES, METHOD OF MAKING, AND METHOD OF USE THEREOF

CROSS-REFERENCE TO RELATED APPLICATIONS

This application is a divisional of and claims priority to U.S. patent application Ser. No. 10/992,805, filed Nov. 19, 2004, which in turn claims the priority of U.S. Patent Application Ser. No. 60/524,099, filed Nov. 21, 2003. Each of the foregoing patent applications is incorporated herein by reference herein in its entirety.

STATEMENT REGARDING FEDERALLY SPONSORED RESEARCH

The U.S. Government has certain rights in this invention pursuant to NSF Grant No. 0111522.

BACKGROUND

This invention relates to certain substituted oxetanes, methods for their production, and therapeutic uses thereof.

Nucleoside analogs play a prominent role in the treatment of cancer, bacterial diseases, fungal diseases, and other pathogenic conditions, including viral diseases such as those arising from the AIDS virus, hepatitis B virus, herpes simplex virus, and cytomegalovirus (CMG). Naturally occurring nucleosides comprise a heterocyclic base, typically guanine, adenine, cytosine, thymine, or uracil, covalently bound to a sugar, typically deoxyribose (DNA nucleosides) or ribose (RNA nucleosides).

After entry into the cell, nucleoside analogs may be phosphorylated by nucleoside salvage pathways, in which the analogs may be phosphorylated to the corresponding mono-, di-, and triphosphates. Triphosphorylated nucleoside analogs, for example, can be strong polymerase inhibitors that can induce premature termination of a nascent nucleic acid molecule, or can act as a substrate for DNA or RNA polymerases and be incorporated into DNA or RNA. When triphosphorylated nucleoside analogs are incorporated into nucleic acid replicates or transcripts, gene expression or disruption of function may result. Nucleoside analogs can thus interfere with the cell cycle, and especially desirable effects of nucleoside analogs include induction of apoptosis of cancer cells. Furthermore, nucleoside analogs are also known to modulate certain immune responses.

Nucleoside analogs having an oxetane ring in place of the sugar moiety include, for example, oxetanocin, which has potent anti-HIV activity in vitro.

Oxetanocin

Other oxetanocin-related compounds are described, for example, in U.S. Pat. No. 5,041,447 to Saito et al. A common feature of oxetanocin and oxetanocin analogs is the presence of a hydrogen on C-2 of the oxetane ring. As there remains a need in the art for improved oxetane-based nucleoside analogs, there accordingly remains a particular need for non-reducing analogs that are fully substituted at C-2 of the oxetane ring. There further remains a need for nucleoside analogs that are more potent, have improved bioavailability, improved stability, improved ease of manufacture, lower toxicity, that do not lead to the development of resistant strains, or a combination of the foregoing.

BRIEF SUMMARY OF THE INVENTION

A composition comprises an oxetane of Formula 1, $$(1)$$

a pharmaceutically acceptable salt, hydrate, solvate, crystal form, diastereomer, prodrug, or mixture thereof wherein:

B is a purin-9-yl, a heterocyclic isostere of a purin-9-yl, a pyrimidin-1-yl, a heterocyclic isostere of a pyrimidin-1-yl, pyrazolyl, substituted pyrazolyl, imidazolyl, substituted imidazolyl, benzimidazolyl, 1,2,3-triazolyl, substituted 1,2,3-triazolyl, benzo-1,2,3-triazolyl, 1,2,4-triazolyl, benzo-1,2,4-triazolyl, pyrrolyl, substituted pyrrolyl, or tetrazolyl; and $R^1$, $R^2$, $R^3$, $R^4$, and $R^5$ are each independently hydrogen;

hydroxy;

amino;

azido;

nitro;

cyano;

halogen;

sulfonamide;

—COOR$^6$ wherein R$^6$ is hydrogen or $C_1$-$C_{12}$ alkyl;

—CONR$^7$R$^8$ wherein R$^7$ and R$^8$ are each independently hydrogen or $C_1$-$C_{12}$ alkyl;

straight or branched $C_1$-$C_{12}$ alkyl wherein the branched alkyl chains may form a 3 to 7 member heteroalkyl ring, alkyl ring, or alkenyl ring, and wherein the straight or branched $C_1$-$C_{12}$ alkyl is optionally substituted with a hydroxy, halogen, COOR$^6$ wherein R$^6$ is defined above, CONR$^7$R$^8$ wherein R$^7$ and R$^8$ are defined above, cyclo($C_3$-$C_6$ alkyl)methyl, —OR$^9$ wherein R$^9$ is $C_1$-$C_6$ alkyl, $C_1$-$C_6$ perhaloalkyl, phenyl, benzyl, or heterocyclic, —SR$^9$, —OR$^{10}$OR$^9$ wherein R$^{10}$ is $C_1$-$C_6$ alkylene, $C_1$-$C_6$ perhaloalkylene, phenyl, or heterocyclic and R$^9$ is as defined above, $C_1$-$C_6$ perhaloalkyl, —NR$^{11}$R$^{12}$ wherein R$^{11}$ and R$^{12}$ are independently hydrogen or $C_1$-$C_6$ alkyl, —NHC(O)R$^{13}$ wherein R$^{13}$ is hydrogen, $C_1$-$C_6$ alkyl, carboxyalkyl, or aminoalkyl, —NC(=NR$^{14}$)NR$^{15}$ wherein R$^{14}$ and R$^{15}$ are each independently hydrogen or $C_1$-$C_6$ alkyl, —N(R$^{16}$)OR$^{17}$ wherein R$^{16}$ and R$^{17}$ are each independently hydrogen or $C_1$-$C_6$ alkyl, —N(R$^{18}$)NR$^{19}$R$^{20}$ wherein R$^{18}$, R$^{19}$, and R$^{20}$ are each independently hydrogen or $C_1$-$C_6$ alkyl;

$C_1$-$C_{12}$ perhaloalkyl;

—OR$^9$ wherein R$^9$ is as defined above;

—SR$^9$ wherein R$^9$ is as defined above;

—O—R$^{10}$OR$^9$ wherein R$^9$ and R$^{10}$ are as defined above;

—NR$^{11}$R$^{12}$ wherein R$^{11}$ and R$^{12}$ are as defined above;

—N(R$^8$)NR$^{19}$R$^{20}$ wherein R$^{18}$, R$^{19}$, and R$^{20}$ are as defined above; or phenyl, —O(phenyl), —O(benzyl), heterocyclic, or —O(heterocyclic) group which may be unsubstituted, or mono-, di-, or trisubstituted with one or more of hydroxy, amino, —NHC(O)R$^{13}$ wherein R$^{13}$ is defined above, azido, nitro, cyano, halogen, sulfonamide, —COOR$^6$ wherein R$^6$ is defined above, —CONR$^7$R$^8$ wherein R$^7$ and R$^8$ are defined above, C$_1$-C$_6$ alkyl, C$_1$-C$_6$ perfluoroalkyl, —OR$^9$ wherein R$^9$ is as defined above, —SR$^9$, —NR$^{11}$R$^{12}$ wherein R$^{11}$ and R$^{12}$ are as defined above, or —N(R$^{18}$)NR$^{19}$R$^{20}$ wherein R$^{18}$, R$^{19}$, and R$^{20}$ are as defined above;

wherein any two of R$^1$, R$^2$, R$^3$, R$^4$, and R$^5$ may form a substituted or unsubstituted 5 to 7 member carbocyclic ring or a substituted or unsubstituted 5 to 7 member heterocyclic ring wherein the substitution is hydroxy, amino, nitro, halogen, sulfonamide, —COOR$^6$, —CONR$^7$R$^8$, cyclo(C$_3$-C$_6$ alkyl) methyl, C$_1$-C$_6$ alkyl, C$_1$-C$_6$ perfluoroalkyl, —OR$^9$, —SR$^9$, —OR$^{10}$OR$^9$, —NR$^{11}$R$^{12}$, —NHC(O)R$^3$, —NC(=NR$^{14}$) NR$^{15}$, —N(R$^{16}$)OR$^{17}$, or —N(R$^{18}$)NR$^{19}$R$^{20}$ wherein R$^6$ to R$^{20}$ are defined above; and with the proviso that at least one of R$^2$, R$^3$, R$^4$ and R$^5$ is not hydrogen; and when R$^2$ and R$^4$ are both hydrogen and either R$^3$ or R$^5$ is C$_1$ alkyl substituted with a hydroxy or —O-benzyl group and the other R$^3$ or R$^5$ is hydrogen, then B is not purin-9-yl-6-amine.

In another embodiment, a pharmaceutical composition comprises a therapeutically effective amount of a compound of Formula 1, a pharmaceutically acceptable salt, hydrate, solvate, crystal form, diastereomer, prodrug, or mixture thereof and a pharmaceutically acceptable carrier.

In still another embodiment, a method of treating a nucleoside analog responsive disorder in a subject comprises administration to the subject a pharmaceutical composition comprising a therapeutically effective amount of a compound of Formula 1, a pharmaceutically acceptable salt, hydrate, solvate, crystal form, diastereomer, prodrug, or a mixture thereof.

DETAILED DESCRIPTION OF THE INVENTION

The compounds of Formula 1 are novel compounds belonging to the family of oxetane-containing nucleosides, and are in particular non-reducing psiconucleoside oxetanes. Without wishing to be bound by theory, it is hypothesized that certain compounds of Formula 1 can interact with DNA to reduce cell proliferation, and thus find utility in therapeutic applications where nucleic acid replication is involved. Compounds of Formula 1 may have therapeutic activity in the treatment of nucleoside analog related disorders such as disorders involving cellular proliferation and infections.

In Formula 1, B is a heterocyclic base, preferably one capable of Watson-Crick binding with DNA or RNA. Suitable heterocyclic bases include, for example, purin-9-yl, pyrimidin-1-yl or pyrimidin-3-yl, and their heterocyclic isosteres, pyrazolyls, imidazolyls, 1,2,3-triazolyls, 1,2,4-triazolyls, or tetrazolyls. The term "heterocyclic isostere" of a purin-9-yl group, e.g., as used herein refers to a heterocyclic group that has a similar structure and similar properties when compared to a purin-9-yl group. In addition, the isostere may contain different atoms and not necessarily the same number of atoms as long as the isostere possesses the same total or valence electrons in the same arrangement as does a purin-9-yl group.

Heterocyclic isosteres of a purin-9-yl group include, for example, compounds of the Formulas (2)-(13):

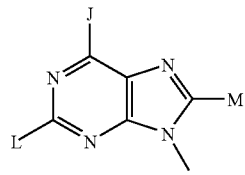

(2)

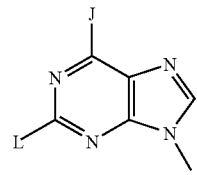

(3)

(4)

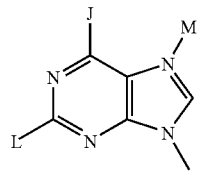

(5)

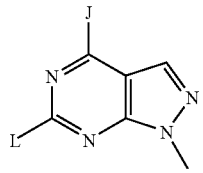

(6)

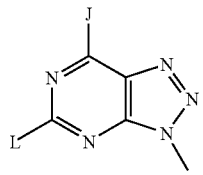

(7)

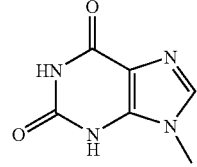

(8)

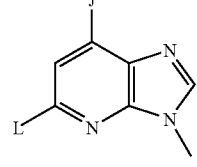

(9)

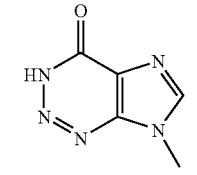

-continued

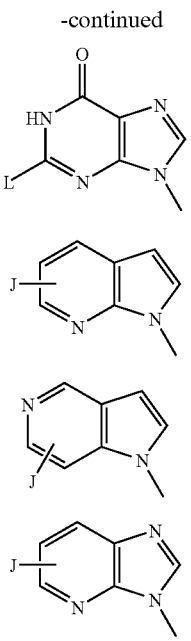

(10)

(11)

(12)

(13)

wherein J, L, and M are each independently
  hydrogen;
  hydroxy;
  halogen;
  $C_1$-$C_{12}$ alkyl;
  $C_1$-$C_6$ perhaloalkyl;
  azido;
  cyano;
  —COOR$^{21}$ wherein R$^{21}$ is hydrogen or $C_1$-$C_{12}$ alkyl;
  —CONR$^{22}$R$^{23}$ wherein R$^{22}$ and R$^{23}$ are each independently hydrogen or $C_1$-$C_{12}$ alkyl;
  —OR$^{24}$ wherein R$^{24}$ is $C_1$-$C_6$ alkyl, $C_1$-$C_6$ perhaloalkyl, phenyl, benzyl, or heterocyclic;
  —SR$^{25}$ wherein R$^{25}$ is hydrogen, $C_1$-$C_6$ alkyl, $C_1$-$C_6$ perhaloalkyl, phenyl, benzyl, or heterocyclic;
  —NR$^{26}$R$^{27}$ wherein R$^{26}$ and R$^{27}$ are independently hydrogen or $C_1$-$C_{12}$ alkyl;
  —SO$_2$NR$^{16}$R$^{27}$ wherein R$^{26}$ and R$^{27}$ are defined above;
  —NHC(O)R$^{28}$ wherein R$^{28}$ is hydrogen, $C_1$-$C_{12}$ alkyl, carboxyalkyl, or aminoalkyl;
  —NC(=NR$^{29}$)NR$^{30}$ wherein R$^{29}$ and R$^{30}$ are each independently hydrogen or $C_1$-$C_{12}$ alkyl;
  —N(R$^{31}$)OR$^{32}$ wherein R$^{31}$ and R$^{32}$ are each independently hydrogen or $C_1$-$C_{12}$ alkyl;
  —N(R$^{33}$)NR$^{34}$R$^{35}$ wherein R$^{33}$, R$^{34}$, and R$^{35}$ are each independently hydrogen or $C_1$-$C_{12}$ alkyl;
  hydroxyamino;
  phenyl, —O(phenyl), benzyl, —O(benzyl), heterocyclic or —O(heterocyclic) group which may be unsubstituted, or mono-, di- or trisubstituted with one or more of hydroxy, amino, azido, nitro, cyano, halogen, sulfonamide, carboxyl, $C_1$-$C_6$ alkyl, $C_1$-$C_6$ perfluoroalkyl, —OR$^{24}$ wherein R$^{24}$ is as defined above, —NR$^{26}$R$^{27}$ wherein R$^{26}$ and R$^{27}$ are as defined above, —N(R$^{33}$)NR$^{34}$R$^{35}$ wherein R$^{33}$, R$^{34}$, and R$^{35}$ are as defined above; or

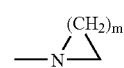

wherein m is 1-5.

In one embodiment, a preferred heterocyclic isostere of a purin-9-yl group includes, for example, compounds of the Formulas (2)-(13), wherein J, L, and M are independently hydrogen, fluoro, chloro, methyl, ethyl, hydroxy, amino, methylamino, dimethylamino.

The term "heterocyclic isostere of a pyrimidin-1-yl group" as used herein refers to a heterocyclic group that has a similar structure and similar properties when compared to a pyrimidin-1-yl group. In addition, the isostere may contain different atoms and not necessarily the same number of atoms as long as the isostere possesses the same total or valence electrons in the same arrangement as does a pyrimidin-1-yl group. Heterocyclic isosteres of a pyrimidin-1-yl group include, for example, compounds of Formulas (14)-(17):

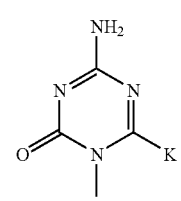

(14)

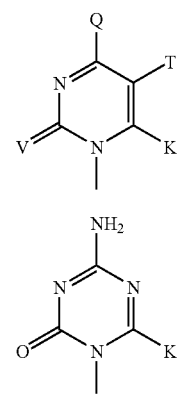

(15)

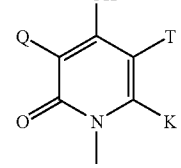

(16)

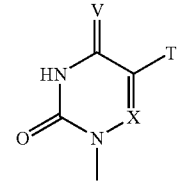

(17)

wherein
  V is O or S;
  X is C or N;
  Q, T, or K are each independently
  hydrogen;
  hydroxy;
  halogen;
  cyano;
  azido;
  nitro;
  hydroxyamino;

—COOR$^{36}$ wherein R$^{36}$ is hydrogen or C$_1$-C$_{12}$ alkyl;

—CONR$^{37}$R$^{38}$ wherein R$^{37}$ and R$^{38}$ are each independently hydrogen or C$_1$-C$_{12}$ alkyl;

—OR$^{39}$ wherein R$^{39}$ is C$_1$-C$_6$ alkyl, C$_1$-C$_6$ perhaloalkyl, phenyl, benzyl, or heterocyclic;

—SR$^{39}$ wherein R$^{39}$ is hydrogen, C$_1$-C$_6$ alkyl, C$_1$-C$_6$ perhaloalkyl, phenyl, benzyl, or heterocyclic;

phenyl, —O(phenyl), benzyl, —O(benzyl), heterocyclic or —O(heterocyclic) group which may be unsubstituted, or mono-, di- or trisubstituted with one or more of hydroxy, amino, azido, nitro, cyano, halogen, sulfonamide, carboxyl, C$_1$-C$_6$ alkyl, C$_1$-C$_6$ perfluoroalkyl, —OR$^{39}$, —SR$^{39}$ wherein R$^{39}$ is as defined above, —NR$^{40}$R$^{41}$ wherein R$^{40}$ and R$^{41}$ are independently hydrogen or C$_1$-C$_{12}$ alkyl, —N(R$^{42}$)NR$^{43}$R$^{44}$ wherein R$^{42}$, R$^{43}$, and R$^{44}$ are each independently hydrogen or C$_1$-C$_{12}$ alkyl;

—NR$^{40}$R$^{41}$ wherein R$^{40}$ and R$^{41}$ are as defined above;

—NHC(O)R$^{42}$ wherein R$^{42}$ is hydrogen, C$_1$-C$_{12}$ alkyl, carboxyalkyl, or aminoalkyl;

straight or branched C$_1$-C$_{12}$ alkyl which is optionally substituted with a hydroxy or halogen and in which the branched alkyl chains may form a 3 to 7 member heteroalkyl, alkyl ring, or alkenyl ring;

C$_1$-C$_{12}$ alkenyl;

C$_1$-C$_{12}$ alkynyl;

—CH$_2$NR$^{43}$R$^{44}$ wherein R$^{43}$ and R$^{44}$ are independently hydrogen or C$_1$-C$_{12}$ alkyl; or

wherein m is 1-5.

In one embodiment, a preferred heterocyclic isostere of a pyrimidin-1-yl group includes, for example, compounds of the Formulas (14)-(17), wherein V is O or S; Q is hydroxy, amino, methylamino, dimethylamino, hydroxyamino; and T and K are each independently hydrogen, methyl, ethyl, trifluoromethyl, fluoro, chloro, bromo, or iodo.

Bases such as pyrazolyl, substituted pyrazolyl, imidazolyl, substituted imidazolyl, benzimidazolyl, 1,2,3-triazolyl, substituted 1,2,3-triazolyl, benzo-1,2,3-triazolyl, 1,2,4-triazolyl, pyrrolyl, substituted pyrrolyl, or tetrazolyl include those of the following Formulas (18)-(21):

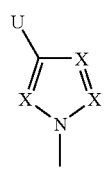

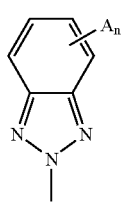

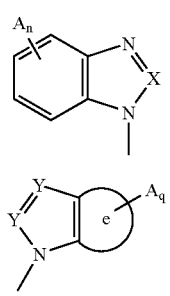

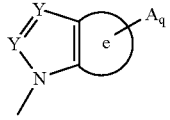

wherein X is C—U or N;

each occurrence of U and A are hydrogen;

hydroxy;

halogen;

C$_1$-C$_{12}$ alkyl;

C$_1$-C$_6$ perhaloalkyl;

azido;

—COOR$^{45}$ wherein R$^{45}$ is hydrogen or C$_1$-C$_{12}$ alkyl;

—CONR$^{46}$R$^{47}$ wherein R$^{46}$ and R$^{47}$ are each independently hydrogen or C$_1$-C$_{12}$ alkyl;

—OR$^{48}$ wherein R$^{48}$ is C$_1$-C$_6$ alkyl, C$_1$-C$_6$ perhaloalkyl, phenyl, benzyl, or heterocyclic;

—SR$^{48}$ wherein R$^{48}$ is defined above;

—NR$^{49}$R$^{50}$ wherein R$^{49}$ and R$^{50}$ are independently hydrogen or C$_1$-C$_{12}$ alkyl;

—NHC(O)R$^{51}$ wherein R$^{51}$ is hydrogen, C$_1$-C$_{12}$ alkyl, carboxyalkyl, or aminoalkyl;

—NC(=NR$^{52}$)NR$^{53}$ wherein R$^{52}$ and R$^{53}$ are each independently C$_1$-C$_{12}$ alkyl;

—N(R$^{54}$)OR$^{55}$ wherein R$^{54}$ and R$^{55}$ are each independently hydrogen or C$_1$-C$_{12}$ alkyl;

—N(R$^{56}$)NR$^{57}$R$^{58}$ wherein R$^{56}$, R$^{57}$, and R$^{58}$ are each independently hydrogen or C$_1$-C$_{12}$ alkyl; or hydroxyamino;

n is 1-4;

e is a five-, six-, or seven-member cycloalkyl or heteroalkyl ring containing 0, 1 or 2 nitrogen atoms in the heteroalkyl ring;

each occurrence of Y is C or N; and q is 0, 1, or 2.

In one embodiment, preferred pyrazolyl, imidazolyl, benzimidazolyl 1,2,3-triazolyl, benzo-1,2,3-triazolyl, 1,2,4-triazolyl, benzo-1,2,4-triazolyl, or tetrazolyl include those of the following Formulas (18)-(21), wherein U is hydrogen, methyl, ethyl, chloro, fluoro, bromo, iodo, trifluoromethyl, amino, methylamino, or dimethylamino; A is hydrogen, chloro, fluoro, bromo, iodo, trifluoromethyl, amino, methylamino, or dimethylamino, hydroxy, or aminohydroxy; n is 1-4; e is a six- or seven-member heteroalkyl ring containing 0, 1, or 2 nitrogen atoms in the heteroalkyl ring; and q is 0 or 1.

Exemplary structures according to Formula (21) include tetrahydroimidazoyl diazepines; tetrahydrobenzoimidazolyl compounds; tetrahydrocyclopentaimidazolyl compounds; tetrahydroinidolyl compounds; hexahydrocyclohepta[b]pyrrolyl compounds; tetrahydrolpyrrolyl diazepines; racemates, diasteriomers, and enantiomers thereof; and the like. Such structures include, for example:

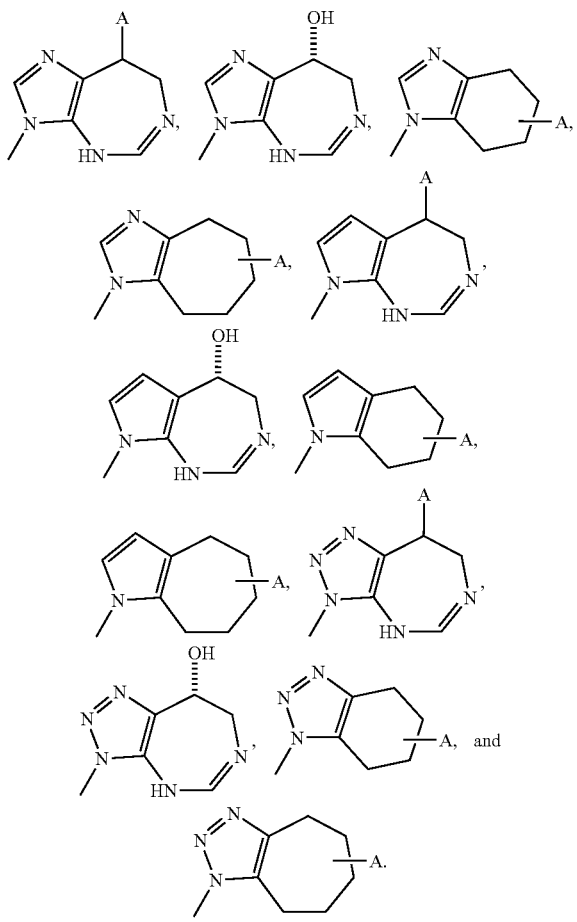

Exemplary bases for B in Formula 1 include, for example, cytosine; adenine; thymine; uracil; benzotriazol-2-yl; 1,2,3-triazol-2-yl; 1,2,3-triazol-1-yl; 1,2,4-triazol-1-yl; tetrazol-2-yl; 5-methylpyrimidin-1-yl-2,4(1H,3H)-dione; 5-ethylpyrimidin-1-yl-2,4(1H,3H)-dione; 5-chloropyrimidin-1-yl-2,4(1H,3H)-dione; 5-fluoropyrimidin-1-yl-2,4(1H,3H)-dione; 5-bromopyrimidin-1-yl-2,4(1H,3H)-dione; 5-iodopyrimidin-1-yl-2,4(1H,3H)-dione; 5-trifluoromethylpyrimidin-1-yl-2,4(1H,3H)-dione; 5-aminopyrimidin-1-yl-2,4(1H,3H)-dione; 5-(methylamino)pyrimidin-1-yl-2,4(1H,3H)-dione; 5-(dimethylamino)pyrimidin-1-yl-2,4(1H,3H)-dione; 5-hydroxypyrimidin-1-yl-2,4(1H,3H)-dione; 1H-purin-9-yl-6(9H)-one, 4-amino-pyrimidin-1-yl-2(1H)-one; 4-amino-5-chloropyrimidin-1-yl-2(1H)-one; 4-amino-5-bromopyrimidin-1-yl-2(1H)-one; 4-amino-5-fluoropyrimidin-1-yl-2(1H)-one; 4-amino-5-iodopyrimidin-1-yl-2(1H)-one; 4-amino-5-methylpyrimidin-1-yl-2(1H)-one; N6-cyclopropyl-9H-purin-9-yl-2,6-diamine; 9H-purin-9-yl-6-amine; 2-amino-1H-purin-9-yl-6(9H)-one; 9H-purin-9-yl-2,6-diamine; 5-amino-1,2,4-triazin-2-yl-3(2H)-one; 5-amino-6-methyl-1,2,4-triazin-2-yl-3(2H)-one; 3,4-dihydro-5-methyl-4-(methylamino)pyrimidin-1-yl-2(1H)-one; 3,4-dihydro-5-chloro-4-(methylamino)pyrimidin-1-yl-2(1H)-one; 3,4-dihydro-5-fluoro-4-(methylamino)pyrimidin-1-yl-2(1H)-one; 3,4-dihydro-5-methyl-4-(hydroxyamino)pyrimidin-1-yl-2(1H)-one; 6-chloro-9H-purin-9-yl, N,-methyl-9H-purin-9-yl-6-amine; and N,N,-dimethyl-9H-purin-9-yl-6-amine.

In a preferred embodiment, $R^1$, $R^2$, $R^3$, $R^4$, and $R^5$ in Formula 1 are each independently hydrogen; a functional group selected from hydroxy, amino, azido, nitro, cyano, halogen, sulfonamide, —COOR$^6$ wherein $R^6$ is hydrogen or $C_1$-$C_{12}$ alkyl, or —CONR$^7$R$^8$ wherein $R^7$ and $R^8$ are each independently hydrogen or $C_1$-$C_{12}$ alkyl; a straight or branched $C_1$-$C_{12}$ alkyl optionally substituted with a hydroxy, halogen, —COOR$^6$ wherein $R^6$ is defined above, —CONR$^7$R$^8$ wherein $R^7$ and $R^8$ are defined above, cyclo($C_3$-$C_6$ alkyl)methyl, —OR$^9$ wherein $R^9$ is $C_1$-$C_6$ alkyl, $C_1$-$C_6$ perhaloalkyl, phenyl, benzyl, or $C_1$-$C_6$ perhaloalkyl; $C_1$-$C_{12}$ perhaloalkyl; —OR$^9$ wherein $R^9$ is as defined above; or phenyl, —O(phenyl), or —O(benzyl), which may be unsubstituted, mono-, di-, or trisubstituted with one or more of hydroxy, amino, azido, nitro, cyano, halogen, sulfonamide, or carboxyl.

In one embodiment, $R^1$ is preferably hydroxy, azido, or fluoro, $R^2$ or $R^4$ is preferably hydrogen, azido, or fluoro, and $R^3$ or $R^5$ is preferably azido, fluoro; straight or branched $C_1$-$C_4$ alkyl optionally substituted with a hydroxy, halogen, carboxyl, cyclo($C_3$-$C_6$ alkyl)methyl, —OR$^9$ wherein $R^9$ is $C_1$-$C_6$ alkyl, $C_1$-$C_6$ perhaloalkyl, phenyl, benzyl, or heterocyclic, —OR$^{10}$R$^9$ wherein $R^{10}$ is $C_1$-$C_6$ alkylene, $C_1$-$C_6$ perhaloalkylene, phenyl, or heterocyclic and $R^9$ is as defined above, $C_1$-$C_6$ perhaloalkyl, —NR$^{11}$R$^{12}$ wherein $R^{11}$ and $R^{12}$ are independently hydrogen or $C_1$-$C_6$ alkyl, —NHC(O)R$^{13}$ wherein $R^{13}$ is hydrogen, $C_1$-$C_6$ alkyl, carboxyalkyl, or aminoalkyl, —NC(=NR$^{14}$)NR$^{15}$ wherein $R^{14}$ and $R^{15}$ are each independently hydrogen or $C_1$-$C_6$ alkyl, —N($R^{16}$)OR)$_7$ wherein $R^{16}$ and $R^{17}$ are each independently hydrogen or $C_1$-$C_6$ alkyl, —N($R^{18}$)NR$^{19}$R$^{20}$ wherein $R^{18}$, $R^{19}$, and $R^{20}$ are each independently hydrogen or $C_1$-$C_6$ alkyl; OR$^9$ wherein $R^9$ is as defined above; or phenyl, —O(phenyl), or —O(benzyl), which may be unsubstituted, mono-, di-, or trisubstituted with one or more of hydroxy, amino, azido, nitro, cyano, halogen, sulfonamide, or carboxyl.

In another embodiment, $R^1$ is preferably hydroxy, azido, chloro, bromo, or fluoro, $R^2$ or $R^4$ is preferably hydrogen, azido, chloro, bromo, or fluoro, and $R^3$ or $R^5$ is preferably azido, fluoro, straight or branched $C_1$-$C_4$ alkyl optionally substituted with a hydroxy, halogen, —OR$^9$ wherein $R^9$ is $C_1$-$C_6$ alkyl, $C_1$-$C_6$ perhaloalkyl, phenyl, benzyl, or heterocyclic, or $C_1$-$C_6$ perhaloalkyl.

In another embodiment, compounds according to Formula (1) is as described above, with the proviso that at least one of $R^2$, $R^3$, $R^4$ and $R^5$ is not hydrogen; and 1) when $R^2$ and $R^4$ are both hydrogen and either $R^3$ or $R^5$ is $C_1$ alkyl substituted with a hydroxy or —O—$R^9$ group, and the other $R^3$ or $R^5$ is hydrogen, then B is not purin-9-yl-6-amine; 2) when either $R^2$ or $R^4$ and either $R^3$ or $R^5$ are $C_1$ alkyl substituted with a hydroxy or —O-benzyl group, and the other $R^2$ or $R^4$ and $R^3$ or $R^5$ are hydrogen, then B is not 4-aminopyrimidin-1-yl-2-one; 2-amino-purin-9-yl-6-one; 4-amino-5-fluoro-pyrimidin-1-yl-2-one; or purin-9-yl-6-amine; or 3) when $R^3$ and $R^5$ are both hydrogen and when either $R^2$ or $R^4$ is phenyl and the other $R^2$ or $R^4$ is hydrogen, then B is not benzo-1,2,3-triazole; 1,2,3-triazole; tetrazole; or 1,2,4-triazole.

"Alkyl" as used herein refers to straight or branched chain alkyl radicals containing the indicated number of carbon atoms including, for example, methyl, ethyl, isopropyl, n-butyl, isobutyl, sec-butyl, n-pentyl, 1-methylbutyl, 2,3-dimethylbutyl, 2-methylpentyl, 2,2-dimethylpropyl, n-hexyl, n-heptyl, n-octyl, n-nonyl, n-decyl, and the like.

"Halo" or "halogen" as used herein refers to fluoro, chloro, bromo, or iodo.

"Perhaloalkyl" as used herein refers to alkyl groups perhalogenated with fluoro, chloro, bromo, iodo, or a combination of the foregoing halogens.

As used herein "3 to 7 member heteroalkyl ring" refers to a saturated cyclic group containing from 1 to about 3 heteroatoms chosen from N, O, and S, with remaining ring atoms being carbon. Examples include morpholinyl, piperazinyl, piperidinyl, and pyrrolidinyl groups.

As used herein "3 to 7 member alkyl ring" refers to saturated hydrocarbon ring groups. Examples of 3 to 7 member alkyl rings include cyclopropyl, cyclobutyl, cyclopentyl, or cyclohexyl as well as bridged or caged saturated ring groups such as norborane.

As used herein "3 to 7 member alkenyl ring" refers to an unsaturated, but not aromatic, hydrocarbon ring having at least one carbon-carbon double bond. Examples include cyclohexenyl and cyclobutenyl.

"Alkenyl" as used herein, indicates a hydrocarbon chain of either a straight or branched configuration having one or more carbon-carbon double bonds, which may occur at any stable point along the chain. Examples of alkenyl groups include ethenyl and propenyl.

"Alkynyl" as used herein, indicates a hydrocarbon chain of either a straight or branched configuration having one or more triple carbon-carbon bonds that may occur in any stable point along the chain, such as ethynyl and propynyl.

The term "heterocyclic group" indicates a 5-6 membered saturated, partially unsaturated, or aromatic ring containing from 1 to about 4 heteroatoms chosen from N, O, and S, with remaining ring atoms being carbon or a 7-10 membered bicyclic saturated, partially unsaturated, or aromatic heterocylic ring system containing at least 1 heteroatom in the two ring system chosen from N, O, and S and containing up to about 4 heteroatoms independently chosen from N, O, and S in each ring of the two ring system. Unless otherwise indicated, the heterocyclic ring may be attached to its pendant group at any heteroatom or carbon atom that results in a stable stricture. When indicated the heterocyclic rings described herein may be substituted on carbon or on a nitrogen atom if the resulting compound is stable. A nitrogen atom in the heterocycle may optionally be quaternized. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benzo[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples heterocyclic groups include, but are not limited to, phthalazinyl, oxazolyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5-pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, thiazolyl N-oxide, tetrazolyl N-oxide, benzothiopyranyl S-oxide, and benzothiopyranyl S,S-dioxide.

The compounds of Formula 1 contain one or more asymmetric carbon atoms and thus can exist as pure enantiomers, racemates, pure diastereomers, mixtures of diastereomers, diastereomeric racemates, or mixtures of diastereomeric racemates. The present invention includes within its scope all of the isomeric forms. The single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral HPLC column. In addition, compounds with carbon-carbon double bonds may occur in Z- and E-forms, with all isomeric forms of the compounds being included. Furthermore where a compound of Formula 1 exists in various tautomeric forms, the invention is not limited to any one of the specific tautomers, and includes all tautomeric forms of the compound.

The term "substituted", as used herein, means that any one or more hydrogens on the designated atom or group is replaced with a selection from the indicated group, provided that the designated atom's normal valence is not exceeded. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when aminoalkyl is listed as a possible substituent the point of attachment of this substituent to the core structure is in the alkyl portion. A dash ("-") that is not between two letters or symbols is used to indicate a point of attachment for a substituent.

In one embodiment, the oxetane of Formula 1 comprises the following stereochemistry as shown in Formulas 1a or 1b:

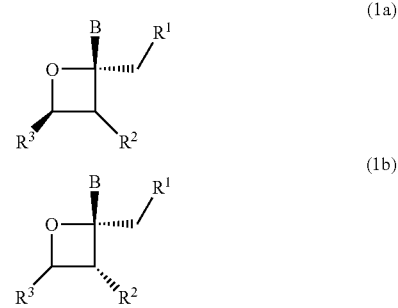

-continued

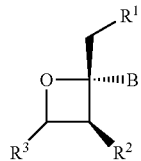
(1c)

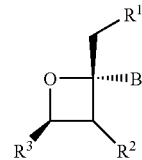
(1d)

($R^4$ and $R^5$ are hydrogen and are not shown).

In one embodiment, compounds according to Formulas 1, 1a, and 1b preferably comprise those set forth in Table 1 below.

TABLE 1

| Compound | B | $R^1$ | $R^2$ | $R^3$ | $R^4$ | $R^5$ |
|---|---|---|---|---|---|---|
| 1 | 2-methyl-1,2,3-triazol-4-yl | —OH | —Ph | —H | —H | —H |
| 2 | " | —OH | —H | —CH$_2$OCH$_2$Ph | —H | —H |
| 3 | " | —OH | —H | —CH$_2$OH | —H | —H |
| 4 | 2-methyltetrazol-5-yl | —OH | —Ph | —H | —H | —H |
| 5 | " | —OH | —H | —CH$_2$OCH$_2$Ph | —H | —H |
| 6 | " | —OH | —H | —CH$_2$OH | —H | —H |
| 7 | 1-methyl-1,2,4-triazol-5-yl | —OH | —Ph | —H | —H | —H |
| 8 | 1-methyl-1,2,3-triazol-5-yl | —OH | —H | —CH$_2$OCH$_2$Ph | —H | —H |
| 9 | " | —OH | —H | —CH$_2$OH | —H | —H |
| 10 | 2-methyl-2H-benzotriazol-4-yl | —OH | —Ph | —H | —H | —H |
| 11 | " | —OH | —H | —CH$_2$OCH$_2$Ph | —H | —H |
| 12 | " | —OH | —H | —CH$_2$OH | —H | —H |

TABLE 1-continued

| Compound | B | R¹ | R² | R³ | R⁴ | R⁵ |
|---|---|---|---|---|---|---|
| 13 | uracil-N1-yl (1-methyl) | —OH | —Ph | —H | —H | —H |
| 14 | tetrazolyl (N-methyl) | —OH | —H | —CH₂OCH₂Ph | —H | —H |
| 15 | tetrazolyl (N-methyl) | —OH | —H | —CH₂OH | —H | —H |
| 16 | benzotriazolyl (N-methyl) | —OH | —H | —CH₂OCH₂Ph | —H | —H |
| 17 | " | —OH | —H | —CH₂OH | —H | —H |
| 18 | 6-chloropurin-9-yl (N-methyl) | —OH | —H | —CH₂OCH₂Ph | —H | —H |
| 19 | " | —OH | —H | —CH₂OH | —H | —H |

The pharmaceutically acceptable acid addition salts of the compounds of Formula 1 are included in the scope of this invention. Non-toxic "pharmaceutically acceptable salts" include, for example salts with inorganic acids, such as hydrochlorate, phosphate, diphosphate, hydrobromate, sulfate, sulfinate, or nitrate salts; or salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH₂)ₙ—COOH where n is 0-4, and the like salts. Similarly, pharmaceutically acceptable cations include, for example sodium, potassium, calcium, aluminum, lithium, and ammonium.

In addition, if the compound of Formula 1 is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts encompassed by Formula 1.

The present invention also encompasses the prodrugs of the compounds of Formula 1, for example acylated prodrugs of the compounds of Formula 1. Those skilled in the art will recognize various synthetic methodologies that may be used to prepare non-toxic pharmaceutically acceptable acylated and other prodrugs of the compounds encompassed by Formula 1.

Methods for obtaining the compounds described herein are known to those of ordinary skill in the art, suitable procedures being described, for example, in the references cited herein, including Taboada R. Ordonio, G., Ndkala, A, Howell, A., and Rablen, P. Journal of Organic Chemistry, Volume 68, pp 1480-88 (2003), which is incorporated herein in its entirety. As described therein, 1,5-dioxaspiro[3.2]hexanes react with nitrogen containing heteroatom compounds to give the ring opened products of alpha-substituted-beta'-hydroxy ketones or 2,2-disubstituted oxetanes. The more acidic heteroatom compounds tended to provide the 2,2-disubstituted oxetanes, the substitutions being a hydroxymethyl and the heteroatom compound. The reaction outcome can further be directed toward the substituted oxetanes by the addition of an appropriate Lewis acid such as, for example, magnesium triflate, zinc chloride, and the like. 1,5-Dioxaspiro[3.2]hexanes can be obtained by the epoxidation of substituted or unsubstituted 2-methylene-oxetane with dimethyldioxirane, for example, to provide an unsubstituted 1,5-dioxaspiro[3.2]hexane or a 1,5-dioxaspiro[3.2]hexane substituted at the 3 and/or the 4 position. Upon ring opening with an appropriate heteroatom nucleophile, the resulting 2-hydroxymethyl may be functionalized or further synthetically manipulated to provide a variety of R¹ groups using techniques well known to one of ordinary skill in the art.

The invention also provides pharmaceutical compositions comprising at least one compound of the invention together with one or more pharmaceutically acceptable carriers and/or diluents and/or adjuvants and if desired other active ingredients. Such pharmaceutical compositions include packaged pharmaceutical compositions for treating disorders responsive to nucleoside analogs. The packaged pharmaceutical compositions include a container holding a therapeutically effective amount of a compound of Formula 1 and instructions (e.g., labeling) indicating that the contained composition is to be used for treating a disorder responsive to a nucleoside analog in the patient. Those skilled in the art will also recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula 1 may be administered orally, topically, parenterally, by inhalation or spray or rectally in dosage unit formulations containing conventional non-toxic pharmaceutically acceptable carriers, adjuvants, and vehicles. Oral administration in the form of a tablet, capsule, elixir, syrup, lozenge, troche, or the like is particularly preferred. The term parenteral as used herein includes subcutaneous injections, intradermal, intravascular (e.g., intravenous), intramuscular, spinal, intrathecal injection, or like injection or infusion techniques. The pharmaceutical compositions containing compounds of general Formula 1 may be in a form suitable for oral use, for example, as tablets, troches, lozenges, aqueous or oily suspensions, dispersible powders or granules, emulsion, hard or soft capsules, syrups or elixirs.

Compositions intended for oral use may be prepared according to methods known in the art for the manufacture of pharmaceutical compositions and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid, or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil, or coconut oil, or in a mineral oil such as liquid paraffin. The oily suspensions may contain a thickening agent, for example beeswax, hard paraffin, or cetyl alcohol. Sweetening agents, such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent, and one or more preservatives. Suitable dispersing or wetting agents and suspending agents are exemplified by those already mentioned above. Additional excipients, for example sweetening, flavoring, and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin, or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol, or sucrose. Such formulations may also contain a demulcent, a preservative, and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution, and isotopic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of general Formula 1 may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials are cocoa butter and polyethylene glycols.

Compounds of general Formula 1 may be administered parenterally in a sterile medium. The drug, depending on the vehicle and concentration used, can either be suspended or dissolved in the vehicle. Advantageously, adjuvants such as local anesthetics, preservatives, and buffering agents can be dissolved in the vehicle.

For administration to non-human animals, the composition may also be added to the animal feed or drinking water. It will be convenient to formulate these animal feed and drinking water compositions so that the animal tales in an appropriate quantity of the composition along with its diet. It will also be convenient to present the composition as a premix for addition to the feed or drinking water.

Dosage levels of the order of from about 0.1 mg to about 140 mg per kilogram of body weight per day are useful in the treatment of the above-indicated conditions (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

Frequency of dosage may also vary depending on the compound used and the particular disease treated. However, for treatment of most disorders, a dosage regimen of 4 times daily or less is preferred. The specific dose level for any particular patient will depend upon a variety of factors, including the activity of the specific compound employed, the age, body weight, general health, sex, diet, time of administration, route of administration, and rate of excretion, drug combination and the severity of the particular disease undergoing therapy.

Preferred compounds have certain pharmacological properties, including for example oral bioavailability, low toxicity, low serum protein binding, and desirable in vitro and in vivo half-lives.

The compounds of this invention may be used in methods of treating a mammal in need of treatment for a disorder responsive to a nucleoside analog such as, for example, a cellular proliferative disease or an infection. The agents are provided in amounts sufficient to modulate a cellular proliferative disease or an infection. Modulation of a cellular proliferative disease can comprise a reduction in tumor growth, inhibition of tumor growth, a chemopotentiator effect, a chemosensitizing effect, cytostasis, a cytotoxic effect, and combinations comprising one or more of the foregoing effects.

A cellular proliferative disease can be a neoplasia. Neoplasias that can be treated include virus-induced tumors, malignancies, cancers or diseases which result in a relatively autonomous growth of cells. Neoplastic disorders include leukemias, lymphomas, sarcomas, carcinomas such as a squamous cell carcinoma, a neural cell tumor, seminomas, melanomas, germ cell tumors, undifferentiated tumors, neuroblastomas (which are also considered a carcinoma by some), mixed cell tumors or other malignancies. Neoplastic disorders prophylactically or therapeutically treatable with compositions of the invention include small cell lung cancers and other lung cancers, rhabdomyosarcomas, choriocarcinomas, glioblastoma multiformas (brain tumors), bowel and gastric carcinomas, leukemias, ovarian cancers, prostate cancers, osteosarcomas or cancers which have metastasized. Diseases of the immune system which may be treated include the non-Hodgkin's lymphomas including the follicular lymphomas, adult T and B cell lymphoproliferative disorders such as leukemias and lymphomas, hairy-cell leukemia, hairy leukoplakia, acute myelogenous, lymphoblastic or other leukermias, chronic myelogenous leukemia and myelodysplastic syndromes. Additional diseases which can be treated include breast cell carcinomas, melanomas and hematologic melanomas, ovarian cancers, pancreatic cancers, liver cancers, stomach cancers, colon cancers, bone cancers, squamous cell carcinomas, neurofibromas, testicular cell carcinomas, central nervous system carcinomas, and adenocarcinomas.

The compounds of this invention may also be used in methods for the treatment of cell-proliferative disorders resulting from viral infections. Such disorders include, for example, viral-induced neoplasia such as certain B and T cell lymphoproliferative disorders, Burkitt's lymphoma, leukemias and other cell malignancies.

The compounds of the invention may be used to treat a variety of microorganism infections, for example, bacterial, fungal, yeast, helminth, protozoan, viral, and combinations comprising one or more of the foregoing infections, including treatment of, for example, *Staphylococcus, Steptococcus, Enterohemmorhagic, Clostridium, Neisseria, Helicobacter, Chlamidia, Tinea, Candida, Mycobacterium*, and *Trypanosoma* infections, and combinations comprising one or more of the foregoing infections. Illustrative bacteria include, for example, *Pseudomonas, Eschericlia, Klebsiella, Enterobacter, Proteus, Serratia, Candida, Staphylococci, Streptococci, Chlamydia, Mycoplasma, Bacillus*, and the like. Illustrative fingi include, for example, *Aspergillis, Candida albicans, Cryptococcus neoformans, Coccidioides immitus*, and the like. Illustrative helminths include, for example, *Ascaris, Diphyllobothrium, Gnathostoma, Wuchereria, Brugia, Onchocerca, Loa Loa, Mansonella*, and the like. Illustrative protozoans include, for example, *Plasmodium, Giardia, Trichomonas, Toxoplasma, Leishmania*, and the like.

Illustrative viruses include, for example, influenza viruses, adenoviruses, parainfluenza viruses, Rhinoviruses, respiratory syncytial viruses (RSVs), Herpes viruses, Hepatitis viruses, e.g., Hepatitis B and C viruses, and the like. Types of virus infections and related disorders that can be treated include, for example, infections due to the herpes family of viruses such as EBV (Epstein-Barr virus), CMV (Cytomegalovirus), Herpes Simplex Virus I (HSV I), Herpes Simplex Virus II (HSV I), Varicella-Zoster Virus, and Kaposi's-associated human herpes virus (type 8), human T cell or B cell leukemia and lymphoma viruses, adenovirus infections, hepatitis virus infections, pox virus infections such as smallpox and the like, papilloma virus infections, polyoma virus infections, infections due to retroviruses such as the Human T-lymphotrophic Virus (HTLV) and Human Immunodeficiency Virus (HIV), and infections that lead to cell proliferative disorders such as, for example, Burkitt's lymphoma, EBV-induced malignancies, T and B cell lymhoproliferative disorders and leukemias, and other viral-induced malignancies.

As an antibacterial or an antifungal, the compounds of the invention have particular application in the agricultural sector including use as an herbicide.

The compounds of this invention may be used in methods of treating a mammal in need of treatment for ischemia-related disorders, for example as cerebroprotective and/or cardioprotective agents. The compounds may be used as antinociceptive, antilipolytic, or antipsychotic agents. Still other uses include, for example, treatment of such diseases or disorders as hypertension, epilepsy, pain, diabetes, and inflammation including rheumatoid arthritis.

In the methods of treatment, the compounds of Formula 1 may be combined with other additional therapeutic agents, for example anti-viral agents, anti-bacterial agents, anti-fungal, or anti-cancer agents. Such anti-viral agents include other nucleoside analogs, nonnucleoside reverse transcriptase inhibitors, protease inhibitors, integrase inhibitors, including the following: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Indinavir; Kethoxal; Lamivudine; Lobucavir; Memotine Hydrochloride; Methisazone; Nelfinavir; Nevirapine; Penciclovir; Pirodavir; Ribavirin; Rimantadine Hydrochloride; Ritonavir; Saquinavir Mesylate; Somantadine Hydrochloride; Sorivudine; Statolon; Stavuidine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovuidine; Zinviroxime, integrase inhibitors, and combinations comprising one or more of the foregoing anti-viral agents.

Additional anti-bacterial agents include antibiotics, for example, tetracycline, aminoglycosides, peinicillins, cephalosporins, sulfonamide drugs, chloramphenicol sodium succinate, erythromycin, vancomycin, lincomycin, clindamycin, nystatin, amphotericin B, amantidine, idoxuridine, p-amino salicyclic acid, isoniazid, rifampin, antinomycin D, mithramycin, daunomycin, adriamycin, bleomycin, vinblastine, vincristine, procarbazine, imidazole carboxamide, and the like.

Additional anti-cancer agents include, for example, nitrosourea, cyclophosphamide, doxorubicin, epirubicin, 5-fluorouracil, topotecan and irinotecan, carmustine, estramustine, paclitaxel and its derivatives, and cisplatin, carboplatin, iproplatin and related platinum compounds.

The following illustrative examples are provided to further describe how to male the oxetane compositions and are not intended to limit the scope of the invention.

EXAMPLES

Synthesis of the following intermediate compounds is described below.

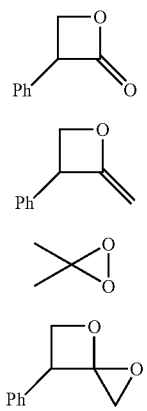

3-Phenyloxetan-2-one (2). Diethylazodicarboxylate (DEAD) (1.89 milliliter (mL), 12.0 millimole (mmol)) was added dropwise to a stirred solution of triphenylphosphine (3.18 gram (g), 12.0 mmol) in dry tetrahydrofuran (THF) (40 mL) at −78° C. under nitrogen (N2). Tropic acid (2.00 g, 12.0 mmol) in dry THF (40 mL) was then added dropwise, and the resulting mixture was stirred and slowly warmed to −10° C., at which point the solution was homogeneous. After concentration and purification by flash chromatography on silica gel (petroleum ether/ethyl acetate (EtOAc) 85:15), 3-phenyloxetan-2-one (1.49 g, 84%) (see Mulzer, J.; Kerkmann, T. J. Am. Chem. Soc. 1980, 102, 3620-3622) was isolated as a yellow oil: $^1$H NMR (270 MHz, CDCl$_3$) δ 7.3 (m, 5H), 4.8 (dd, J=5.0, 1.7 Hz, 1H), 4.5 (dd, J=5.0, 1.7 Hz, 1H), 4.2 (dd, J=5.0, 5.0 Hz, 1H).

2-Methylene-3-phenyloxetane (3). Dimethyltitanocene (0.5 M in toluene, 19.5 mL, 9.7 mmol) and 3-phenyloxetan-2-one (0.96 g, 6.5 mmol) were stirred at 75° C. under N$_2$ in the dark. The reaction was monitored by thin layer chromatography (TLC), and after the disappearance of the lactone (2-15 hours) the solution was cooled and concentrated to half of its original volume. Petroleum ether (20 mL) was then added, at which point a yellow precipitate formed. The mixture was passed through celite with petroleum ether until the filtrate was colorless. After concentration, if large amounts of solid were still present, the mixture was diluted with petroleum ether and filtered through celite a second time. The residue was then purified by flash chromatography on silica gel (petroleum ether/EtOAc/triethylamine 98.5:0.5:1). 2-Methylene-3-phenyloxetane (0.48 g, 51%) was isolated as a pale yellow oil: IR (film) 3100, 3080, 2990, 2900, 1680, 1620, 1500, 1480, 1300 cm$^{-1}$; $^1$H NMR (270 MHz, CDCl$_3$) δ 7.40-7.27 (m, 5H), 4.96 (dd, J=7.5, 5.0 Hz, 1H), 4.67 (m, 1H), 4.57 (dd, J=5.0, 5.0 Hz, 1H), 4.27 (dd, J=3.9, 2.4 Hz, 1H), 3.81 (dd, J=3.9, 1.8 Hz, 1H); $^{13}$C NMR (67.5 MHz, CDCl$_3$) δ 166.4, 138.6, 128.8, 127.4, 127.3, 80.3, 75.9, 47.2,; MS (EI) m/z 146 (M$^+$), 131, 116 (100), 104, 89, 78, 63, 51; HRMS (EI) calculated for C$_{10}$H$_{10}$O (M$^+$) m/z: 146.0732. Found: 146.0737.

Dimethyldioxirane (4). Dimethyldioxirane (DMDO) was prepared as described below, following the procedure of Adam (Adam, W.; Bialas, J.; Hadjiarapoglou, L. Chem. Ber. 1991, 124, 2377) and Murray (Murray, R. W.; Singh, M. Org. Syn. 1996, 74, 91-100), and concentrated as described by Messegeur (Ferrer, M.; Gilbert, M.; Sanches-Baeza, F.; Messeguer, A. Tetrahedron Lett. 1996, 37, 3585-3586). A mixture of NaHCO$_3$ (90 g), water (250 mL) and acetone (200 mL) in a 3 L round-bottomed flask was cooled to 0° C. and oxone added slowly (5 minutes) with stirring. After the addition, the mixture was stirred rapidly for 10 minutes and then a vacuum (80 mm mercury (Hg)) was applied. The cooling bath was removed, and the DMDO in acetone (85 mL) trapped over 1 hour in two receiving flasks connected in series and maintained at −78° C. The trapped solution was diluted with water (85 mL) and extracted with CH$_2$Cl$_2$ (3×4.5 mL). The combined organic extracts were washed with phosphate buffer (pH 7, 3×30 mL). The organic layer was dried (K$_2$CO$_3$), and filtered to give a yellow solution (12 mL). The concentration of DMDO was determined using a GC calibration curve of methyl citronellate, employing octadecane as an internal standard. This determination is based on the reaction of DMDO with excess methyl citronellate. The concentrations of the DMDO obtained varied from 0.30-0.45 M.

3-Phenyl-1,5-dioxaspiro[3.2]hexane (5). A solution of 2-methylene-3-phenyloxetane (0.10 g, 0.69 mmol) in dry CH$_2$Cl$_2$ (~0.5 M) was cooled to −78° C. A solution of DMDO (~0.35 M in CH$_2$Cl$_2$, 1.0-1.2 equiv) was added dropwise with stirring. The reaction mixture was stirred at −78° C. for 1 hour after which the solvent was removed in vacuo to give 3-phenyl-1,5-dioxaspiro[3.2]hexane as a colorless oil (0.11 g, 99%) and as a mixture of diastereomers (93:7). Major diastereomer: $^1$H NMR (400 MHz, CDCl$_3$) δ 7.33 (m, 5H), 4.85 (m, 1H), 4.49 (m, 2H), 2.93 (d, J=3.4 Hz, 1H), 2.54 (d, J=3.4 Hz, 1H); $^{13}$C NMR (100 MHz, CDCl$_3$) δ 136.6, 128.9, 127.8, 127.5, 95.0, 70.1, 50.5, 47.9. Minor diastereomer: ¹H NMR (400 MHz, CDCl₃) δ 7.33 (m, 5H), 4.85 (m, 1H), 4.65 (app t, J=6.6 Hz, 1H), 4.58 (dd, J=6.3, 5.0 Hz, 1H), 3.06 (d, J=3.4 Hz, 1H), 2.76 (d, J=3.4 Hz, 1H); ¹³C NMR (100 MHz, CDCl₃) δ 135.5, 129.3, 128.6, 128.2, 92.7, 72.0, 51.4, 46.7; HRMS (FAB) calculated for C₁₀H₁₁O₂ (M⁺+1) m/z: 163.0759. Found: 163.0762.

Synthesis of the following compounds in accordance with the present invention is shown below:

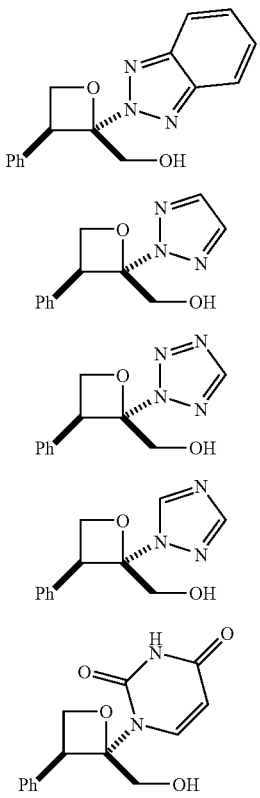

Example 1

2-(Benzotriazol-2-yl)-2-(hydroxymethyl)-3-phenyloxetane (6). Benzotriazole (0.15 g, 1.3 mmol) in dry CH₂Cl₂ (4 mL) at 0° C. was added to a stirred solution under N₂ of 3-phenyl-1,5-dioxaspiro[3.2]hexane (0.21 g, 1.3 mmol) in dry CH₂Cl₂ (4 mL) at 0° C. The reaction mixture was left to stir for 3 hours at 0° C. It was then concentrated to provide a light brown oil. The residue was purified by flash chromatography on silica gel (petroleum ether/EtOAc 80:20) to give 2-(benzotriazol-2-yl)-2-(hydroxymethyl)-3-phenyloxetane as a white solid (0.15 g, 41%): mp 119-123° C.; IR (film) 3437 (br), 3094, 3064, 2941, 1560, 1499 cm⁻¹; ¹H NMR (400 MHz, CDCl₃) δ 7.95 (d, J=8.1 Hz, 2H), 7.35 (m, 7H), 5.42 (dd, J=8.7, 7.0 Hz, 1H), 5.20 (dd, J=8.7, 6.0 Hz, 1H), 5.09 (dd, J=6.8, 6.0 Hz, 1H), 4.25 (dd, J 13.0, 7.7 Hz, 1H), 4.20 (dd, J=13.0, 7.0 Hz, 1H), 2.6 (dd, J=7.3, 7.3 Hz, 1H); ¹³C NMR (100 MHz, CDCl₃) δ 144.8, 134.3, 129.3, 128.6, 128.5, 127.8, 119.1, 102.2, 69.8, 63.8, 48.8; MS (EI) m/z 281 (M⁺), 251, 162, 104 (100), 91; HRMS (FAB) calculated for C₁₆H₁₆N₃O₂ (M⁺+H) m/z 282.1242. Found: 282.1248; Anal. calculated for C₁₆H₁₅N₃O₂: C, 68.31; H, 5.37; N, 14.94. Found: C, 68.13; H, 5.40; N, 14.97.

Example 2

2-Hydroxymethyl-3-phenyl-2-(1,2,3-triazol-2-yl)oxetane (7). A solution of 1H-1,2,3-triazole (0.043 g, 0.62 mmol) in dry CH₂Cl₂ (2 mL) was introduced to a stirred solution under N₂ of 3-phenyl-1,5-dioxaspiro[3.2]hexane (0.10 g, 0.62 mmol) in dry CH₂Cl₂ (2 mL) at −78° C. After 3 hours at −78° C., the reaction was allowed to warm to room temperature; then, the solvent was evaporated in vacuo. The resultant oil was purified by flash chromatography on silica gel (CH₂Cl₂/EtOAc 95:5). 2-Hydroxymethyl-3-phenyl-2-(1,2,3-triazol-2-yl)oxetane was isolated as a pale yellow solid (0.076 g, 59%): mp 77.0-78.3° C.; IR (CDCl₃) 3145, 3031, 2969, 1496, 1452, 1323, 1049 cm⁻¹; ¹H NMR (400 MHz, CDCl₃) δ 7.82 (s, 2H), 7.41 (m, 2H), 7.35 (m, 3H), 5.41 (dd, J=8.2, 7.7 Hz, 1H), 5.08 (dd, J=8.5, 6.0 Hz, 1H), 4.98 (dd, J=7.0, 6.0 Hz, 1H), 4.15 (dd, J=13.0, 7.6 Hz, 1H), 4.10 (dd, J=13.0, 7.6 Hz, 1H), 2.51 (t, J=7.6 Hz, 1H); ¹³C NMR (100 MHz, CDCl₃) δ 135.3, 134.1, 128.8, 128.1, 128.0, 99.7, 68.5, 62.9, 47.9; MS (EI) m/z 200 (M⁺-CH₂O), 185, 104 (100), 78; Anal. calculated for C₁₂H₁₃N₃O₂: C, 62.33; H, 5.67; N, 18.17. Found: C, 62.58; H, 5.30; N, 17.94.

Example 3

2-Hydroxymethyl-3-phenyl-2-(tetrazol-2-yl)oxetane (8). 1H-Tetrazole (0.078 g, 1.1 mmol) in dry THF (2 mL) was added dropwise to a stirred solution under N₂ of 3-phenyl-1,5-dioxaspiro[3.2]hexane (0.15 g, 0.94 mmol) in dry THF (2 mL) at 0° C. The reaction mixture was stirred for 1 hour and then concentrated. The resultant yellow oil was purified by flash chromatography on silica gel (CH₂Cl₂/methanol 100:0 to 98:2) to provide 2-hydroxymethyl-3-phenyl-2-(tetrazol-2-yl)oxetane as a pale yellow oil (0.090 g, 42%): IR (CDCl₃) 3436 (br), 2916, 1319, 1054, 953 cm⁻¹; ¹H NMR (400 MHz, CDCl₃) δ 8.70 (s, 1H), 7.42 (m, 5H), 5.37 (dd, J=8.6, 6.9 Hz, 1H), 5.16 (dd, J=8.6, 6.1 Hz, 1H), 5.08 (dd, J=6.2, 6.2 Hz, 1H), 4.21 (dd, J=13.5, 7.5 Hz, 1H), 4.17 (dd, J=13.5, 7.4 Hz, 1H), 1.86 (dd, J=7.4, 7.4 Hz, 1H); ¹³C NMR (100 MHz, CDCl₃) δ 153.1, 133.2, 129.1, 128.5, 128.1, 100.9, 69.6, 62.6, 47.8; MS (EI) m/z 204 (M+—N₂), 185, 173, 104 (100), 91, 78; Anal. calculated for C₁₁H₁₂N₄O₂: C, 56.89; H, 5.21; N, 24.12. Found: C, 56.76; H, 5.14; N, 23.78.

Example 4

2-Hydroxymethyl-3-phenyl-2-(1,2,4-triazol-1-yl)oxetane (9). A solution of magnesium triflate (0.40 g, 1.23 mmol) in dry THF (5 mL) was added to a stirred solution under N₂ of 3-phenyl-1,5-dioxaspiro[3.2]hexane (0.20 g, 1.23 mmol) in dry THF (2 mL). The temperature was then lowered to 0° C., and a solution of 1H-1,2,4-triazole (0.22 g, 1.48 mmol) in dry THF (10 mL) was added dropwise. The reaction mixture was stirred at 0° C. for 2.5 hours, warmed to room temperature and stirred for an additional 3 hours. Then, the mixture was concentrated to provide a yellow oil, which was purified by flash chromatography on silica gel (CH₂Cl₂/methanol 99.5:0.5 to 99:1). 2-Hydroxymethyl-3-phenyl-2-(1,2,4-triazol-1-yl)oxetane was isolated as an oil which was a 2:1 mixture of diastereomers (0.13 g, 45%): IR (film) 3403, 2903, 1499, 1279, 702 cm⁻¹; Major diastereomer: ¹H NMR (400 MHz, CDCl₃) δ 8.18 (s, 1H), 8.11 (s, 1H), 7.40 (m, 5H), 5.11 (m, 1H), 5.06 (m, 1H), 4.74 (dd, J=16.3, 8.4 Hz, 1H), 3.94 (d, J=12.8 Hz, 1H), 3.83 (d, J=12.8 Hz, 1H); ¹³C NMR (100 MHz, CDCl₃) δ 133.3, 129.0, 127.9, 127.7, 127.4, 127.4, 98.5, 68.9, 63.7, 48.7. Minor diastereomer: ¹H NMR (400 MHz, CDCl₃) δ 8.42 (s, 1H), 7.67 (s, 1H), 7.12 (m, 5H), 5.11

(m, 1H), 5.06 (m, 1H), 4.74 (dd, J=16.3, 8.4 Hz, 1H), 4.75 (d, J=12.8 Hz, 1H), 4.31 (d, J=12.8 Hz, 1H); $^{13}$C NMR (100 MHz, CDCl$_3$) δ 133.3, 129.0, 127.9, 127.7, 127.4, 127.4, 98.5, 70.6, 67.2, 45.8; MS (EI) m/z 167, 149 (100), 71; HRMS (FAB) calculated for C$_{12}$H$_{14}$N$_3$O$_2$ (M$^+$+H) m/z 232.1086. Found: 232.1101.

Example 5

1-(2-Hydroxymethyl-3-phenyloxetan-2-yl)-3H-pyrimidine-2,4-dione (10). A solution of persilylated uracil (0.100 g, 0.40 mmol) (see Kato, K.; Chen, C. Y.; Akita, H. *Synthesis* 1998, 1527-1533) in CH$_2$Cl$_2$ (1 mL) was added dropwise to a slurry under N$_2$ of 3-phenyl-1,5-dioxaspiro[3.2]hexane (0.025 g, 0.15 mmol) and zinc chloride (0.021 g, 0.15 mmol) in dry CH$_2$Cl$_2$ (2 mL) at −78° C. The reaction mixture was stirred at −78° C. for 6 hours, and it was then gradually allowed to warm to room temperature. Subsequently, the reaction mixture was diluted with CH$_2$Cl$_2$ (10 mL), washed with 6% NH$_4$Cl (10 mL), brine (10 mL), and dried (MgSO$_4$). The solvent was evaporated in vacuo, and the residue was purified by flash chromatography on silica gel (CH$_2$Cl$_2$/methanol 100:0 to 95:5). 1-(2-Hydroxymethyl-3-phenyloxetan-2-yl)-3H-pyrimidine-2,4-dione was isolated as a clear oil (0.023 g, 55%): $^1$H NMR (400 MHz, CDCl$_3$) δ 7.93 (s, 1H), 7.80 (d, J=2.0 Hz, 1H), 7.78 (d, J=2.0 Hz, 1H), 7.65 (m, 5H), 5.74 (m, 1H), 5.04 (m, 1H), 4.59 (m, 1H), 4.38 (d, J=11.1 Hz, 1H), 4.13 (d, J=11.1 Hz, 1H).

Synthesis of the following intermediate compounds is described below.

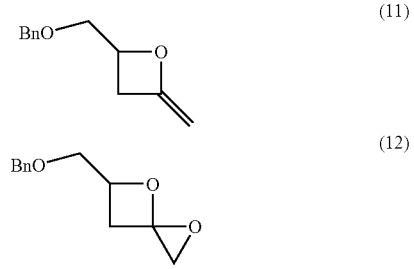

Example 6

4-Benzyloxymethyl-2-methyleneoxetane (11). A solution of dimethyltitanocene (0.5M in toluene, 7.8 mL, 3.9 mmol) and 4-(benzyloxylmethyl)oxetan-2-one (0.50 g, 2.6 mmol) (see Nelson, S. G.; Wan, Z.; Peelen, T. J.; Spencer, K. L. *Tetrahedron Lett.* 1999, 40, 6535-6539) was stirred in the dark at 80° C. under N$_2$. The reaction was monitored over a period of 4-6 hours by TLC until the disappearance of the starting material. The cooled reaction mixture was quenched with petroleum ether (8 mL) and stirred for 0.5-1 hour. The yellow precipitate was filtered through a pad of celite and the celite cake was washed with petroleum ether until the filtrate was clear. The filtrate was concentrated in vacuo, and the residue was purified by flash chromatography on silica gel (petroleum ether/EtOAc/triethylamine 99:0.5:0.5). 4-Benzyloxymethyl-2-methyleneoxetane was isolated as a yellow oil (0.22 g, 44%). IR (CDCl$_3$) 3100, 2926, 1691, 1452 cm$^{-1}$; $^1$H NMR (400 MHz, CDCl$_3$) δ 7.35 (m, 3H), 7.28 (m, 2H), 4.92 (dddd, J=9.1, 6.9, 5.1, 5.1 Hz, 1H), 4.66 (d, J=12.0 Hz, 1H), 4.62 (d, J=12.0 Hz, 1H), 4.16 (m, 1H), 3.78 (ddd, J=3.5, 1.7, 1.7 Hz, 1H), 3.71 (dd, J=11.3, 5.2 Hz, 1H), 3.70 (dd, J=11.3, 4.0 Hz, 1H), 3.20 (dddd, J=6.9, 6.9, 1.8, 1.8 Hz, 1H), 3.03 (dddd, J=4.6, 4.6, 2.0, 2.0 Hz, 1H); $^{13}$C NMR (100 MHz, CDCl$_3$) δ 163.5, 138.2, 128.7, 128.0, 80.8, 73.9, 71.9, 31.2.

Example 7

2-Benzyloxymethyl-1,5-dioxaspiro[3.2]hexane (12). A solution of 4-benzyloxymethyl-2-methyleneoxetane (0.19 g, 0.98 mmol) in dry CH$_2$Cl$_2$ (2 mL), was cooled to −78° C. Dimethyldioxirane (0.5M in CH$_2$Cl$_2$, 2 eq) was added dropwise to the stirred solution. The reaction mixture was stirred for 1 hour more, then quickly warmed to room temperature, and, subsequently, the solvent was removed in vacuo. 2-Benzyloxymethyl-1,5-dioxaspiro[3.2]hexane was isolated as pale yellow oil (0.19 g, 95%) and as a mixture of diastereoisomers (72:28). Major diastereomer: $^1$H NMR (400 MHz, CDCl$_3$) δ 7.30 (m, 5H), 4.83 (m, 1H), 4.67 (d, J=12.2 Hz, 1H), 4.62 (d, J=12.2 Hz, 3H), 3.71 (m, 2H), 3.06 (dd, J=12.6, 2.7 Hz, 1H), 3.04 (dd, J=12.6, 4.2 Hz, 1H), 2.93 (d, J=3.3 Hz, 1H), 2.71 (d, J=3.3 Hz, 1H); $^{13}$C NMR (100 MHz, CDCl$_3$) δ 138.2, 128.6, 127.9, 127.8, 89.0, 73.8, 73.5, 72.1, 51.4, 31.4. Minor diastereomer: $^1$H NMR (400 MHz, CDCl$_3$) δ 7.30 (m, 5H), 4.70 (m, 1H), 3.71 (m, 2H), 3.19 (dd, J=12.6, 7.2 Hz, 1H), 2.94 (d, J=3.6 Hz, 1H), 2.88 (dd, J=12.7, 5.6 Hz, 1H), 2.75 (d, J=3.4 Hz, 1H); $^{13}$C NMR (100 MHz, CDCl$_3$) δ 138.2, 128.6, 127.9, 127.8, 88.2, 73.9, 72.6, 72.5, 51.3, 31.6.

Synthesis of the following compounds in accordance with the present invention is shown below:

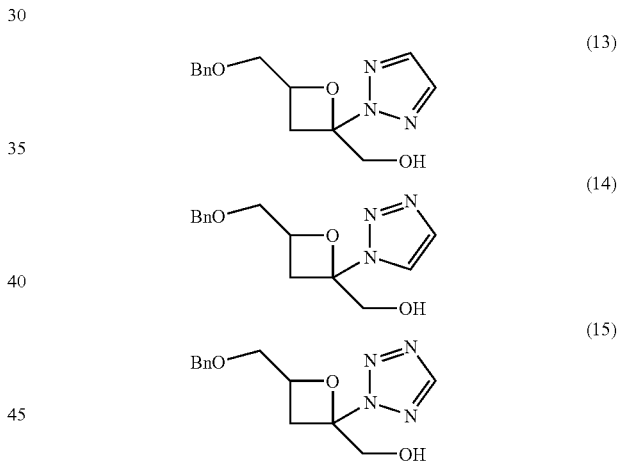

Examples 8 and 9

4-Benzyloxymethyl-2-hydroxymethyl-2-(1,2,3-triazol-2-yl)oxetane (13) and 4-benzyloxymethyl-2-hydroxymethyl-2-(1,2,3-triazol-1-yl)oxetane (14). A solution of 1H-1,2,3-triazole (0.018 g, 0.26 mmol) in dry CH$_2$Cl$_2$ (2 mL) was introduced to a stirred solution under N$_2$ of 2-benzyloxymethyl-1,5-dioxaspiro[3.2]hexane (0.054 g, 0.26 mmol) in dry CH$_2$Cl$_2$ (2 mL) at −78° C. After 3 hours at −78° C., the reaction was allowed to warm to room temperature; then, the solvent was evaporated in vacuo. The resultant oil was purified by flash chromatography on silica gel (CH$_2$Cl$_2$/MeOH 100:0 to 95:5), followed by preparatory TLC (CH$_2$Cl$_2$/MeOH 96:4). 4-Benzyloxymethyl-2-hydroxymethyl-2-(1,2,3-triazol-2-yl)oxetane and 4-benzyloxymethyl-2-hydroxymethyl-2-(1,2,3-triazol-1-yl)oxetane were isolated as single compounds and as colorless oils: 4-Benzyloxymethyl-2-hydroxymethyl-2-(1,2,3-triazol-2-yl)oxetane: $^1$H NMR (400

MHz, CDCl₃) δ 7.73 (s, 2H), 7.36 (m, 3H), 7.32 (m, 2H), 5.17 (dddd, J=7.4, 7.4, 3.0, 3.0 Hz, 1H), 4.70 (d, J=12.0 Hz, 1H), 4.62 (d, J=12 Hz, 1H), 4.36 (app d, J=12.4 Hz, 1H), 4.17 (dd, J=12.1, 7.2 Hz, 1H), 3.80 (dd, J=11.6, 2.7 Hz, 1H), 3.65 (dd, J=11.6, 3.3 Hz, 1H), 3.40 (d, J=7.5 Hz, 2H), 3.4 (br. s, 1H); ¹³C NMR (100 MHz, CDCl₃) δ 137.7, 135.2, 128.7, 128.2, 128.0, 96.5, 75.8, 73.8, 71.4, 65.7, 30.4. 4-Benzyloxymethyl-2-hydroxymethyl-2-(1,2,3-triazol-1-yl)oxetane: ¹H NMR (400 MHz, CDCl₃) δ 7.93 (s, 1H), 7.76 (s, 1H), 7.35 (m, 5H), 5.01 (dddd, J=7.4, 7.4, 3.0, 3.0 Hz, 1H), 4.69 (d, J=11.9 Hz, 1H), 4.63 (d, J=11.9 Hz, 1H), 4.01 (dd, J=12.0, 6.8 Hz, 1H), 3.91 (app d, J=12.3 Hz, 1H), 3.81 (dd, J=11.5, 2.2 Hz, 1H), 3.66 (dd, 11.4, 3.3 Hz, 1H), 3.48 (dd, J=12.3, 7.1 Hz, 1H), 3.25 (br s, 1H), 3.06 (dd, J=12.5, 7.8 Hz, 1H);); ¹³C NMR (100 MHz, CDCl₃) δ 137.3, 133.9, 128.8, 128.4, 128.2, 121.8, 95.9, 76.4, 73.9, 71.2, 67.1, 30.1.

Example 10

4-Benzyloxymethyl-2-hydroxymethyl-2-(tetrazol-2-yl)oxetane (15). A solution of 4-benzyloxymethyl-2-methyleneoxetane (0.025 g, 0.13 mmol) in CH₂Cl₂ under N₂ was cooled to −78° C. Then, dimethyldioxirane (0.5 M, 0.52 mL, 0.26 mmol) was added dropwise, and the reaction was stirred at −78° C. for 1 h. The solvent was then evaporated to give 2-benzyloxymethyl-1,5-dioxaspiro[3.2]hexane, which was dissolved in dry THF (2 mL). The solution was stirred under N₂ and cooled to 0° C. A solution of 1H-tetrazole (0.01 g, 0.14 mmol) in dry THF (2.0 mL) was added. The reaction mixture was stirred at 0° C. for 3 h and was then warmed to room temperature, followed by removal of the solvent in vacuo. The resultant oil was purified by preparatory TLC on silica gel (CH₂Cl₂/MeOH 96:4). 4-Benzyloxymethyl-2-hydroxymethyl-2-(tetrazol-2-yl)oxetane was isolated as a clear oil was (32 mg, 88% over 2 steps). ¹H NMR (400 MHz, CDCl₃) δ 8.61 (s, 1H), 7.34 (m, 5H), 5.23 (m, 1H), 4.69 (d, J=11.9 Hz, 1H), 4.63 (d, J=11.9 Hz, 1H), 4.40 (app d, J=12.6 Hz, 1H), 4.17 (dd, J=12.2, 8.7 Hz, 1H), 3.83 (dd, J=11.7, 2.2 Hz, 1H), 3.68 (dd, J=11.7, 2.8 Hz, 1H), 3.60 (dd, J=12.3, 7.2 Hz, 1H), 3.40 (dd, J=12.3, 7.6 Hz, 1H), 3.24 (app d, J=5.4 Hz, 1H); ¹³C NMR (100 MHz, CDCl₃) δ 153.4, 137.6, 129.1, 128.6, 128.4, 97.8, 76.8, 74.2, 71.0, 65.4, 30.2; MS (EI) m/z 149, 107, 91 (100), 77, 65.

Examples 11-18

Additional examples prepared in accordance with the procedures above include:

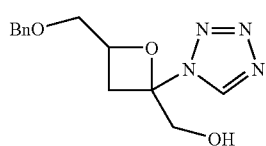
(16)

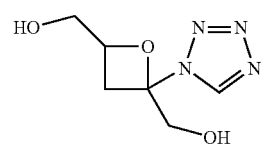
(17)

-continued

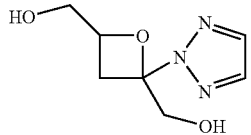
(18)

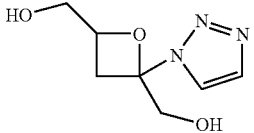
(19)

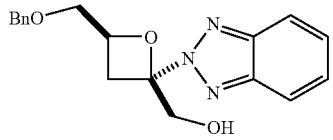
(20)

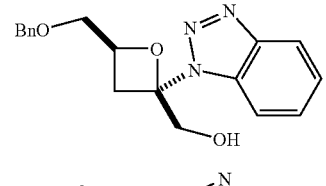
(21)

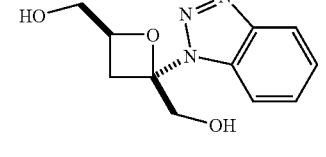
(22)

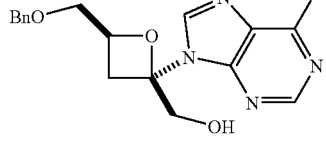
(23)

The essential characteristics of the present invention are described completely in the foregoing disclosure. One skilled in the art can understand the invention and make various modifications without departing from the basic spirit of the invention, and without deviating from the scope and equivalents of the specific embodiments, which follow.

What is claimed is:
1. A compound, comprising:
an oxetane of Formula 1,

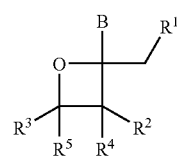
(1)

a pharmaceutically acceptable salt, diastereomer, or mixture thereof wherein:

B is a pyrimidin-1-yl or a heterocyclic isostere of a pyrimidin-1-yl, wherein the pyrimidin-1-yl or heterocyclic isostere of a pyrimidin-1-yl comprises

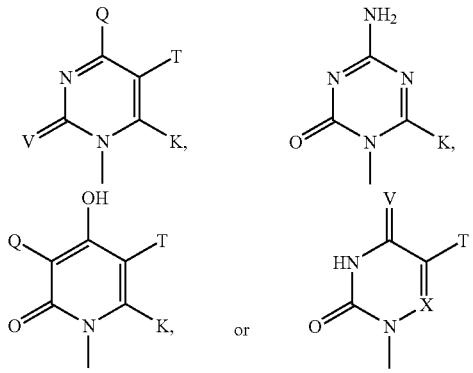

wherein
V is O or S;
X is C or N;
Q, T, or K are each independently
hydrogen;
hydroxy;
halogen;
cyano;
azido;
nitro;
hydroxyamino;
—COOR$^{36}$ wherein R$^{36}$ is hydrogen or C$_1$-C$_{12}$ alkyl;
—CONR$^{37}$R$^{38}$ wherein R$^{37}$ and R$^{38}$ are each independently hydrogen or C$_1$-C$_{12}$ alkyl;
—OR$^{39}$ wherein R$^{39}$ is C$_1$-C$_6$ alkyl, C$_1$-C$_6$ perhaloalkyl, phenyl, benzyl, or heterocyclic;
—SR$^{39}$ wherein R$^{39}$ is hydrogen, C$_1$-C$_6$ alkyl, C$_1$-C$_6$ perhaloalkyl, phenyl, benzyl, or heterocyclic;
phenyl, —O(phenyl), benzyl, —O(benzyl), heterocyclic or —O(heterocyclic) group which may be unsubstituted, or mono-, di- or trisubstituted with one or more of hydroxy, amino, azido, nitro, cyano, halogen, sulfonamide, carboxyl, C$_1$-C$_6$ alkyl, C$_1$-C$_6$ perfluoroalkyl, —OR$^{39}$, —SR$^{39}$ wherein R$^{39}$ is as defined above, —NR$^{40}$R$^{41}$ wherein R$^{40}$ and R$^{41}$ are independently hydrogen or C$_1$-C$_{12}$ alkyl, —N(R$^{42}$)NR$^{43}$R$^{44}$ wherein R$^{42}$, R$^{43}$, and R$^{44}$ are each independently hydrogen or C$_1$-C$_{12}$ alkyl;
—NR$^{40}$R$^{41}$ wherein R$^{40}$ and R$^{41}$ are as defined above;
—NHC(O)R$^{42}$ wherein R$^{42}$ is hydrogen, C$_1$-C$_{12}$ alkyl, carboxyalkyl, or aminoalkyl;
straight or branched C$_1$-C$_{12}$ alkyl which is optionally substituted with a hydroxy or halogen and in which the branched alkyl chains may form a 3 to 7 member heteroalkyl, alkyl ring, or alkenyl ring;
C$_1$-C$_{12}$ alkenyl;
C$_1$-C$_{12}$ alkynyl;
—CH$_2$NR$^{43}$R$^{44}$ wherein R$^{43}$ and R$^{44}$ are independently hydrogen or C$_1$-C$_{12}$ alkyl; or

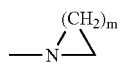

wherein m is 1-5;
wherein R$^2$, R$^3$, R$^4$, and R$^5$ are each independently
hydrogen;
hydroxy;
amino;
azido;
nitro;
cyano;
halogen;
sulfonamide;
—COOR$^6$ wherein R$^6$ is hydrogen or C$_1$-C$_{12}$ alkyl;
—CONR$^7$R$^8$ wherein R$^7$ and R$^8$ are each independently hydrogen or C$_1$-C$_{12}$ alkyl;
straight or branched C$_1$-C$_{12}$ alkyl wherein the branched alkyl chains may form a 3 to 7 member heteroalkyl ring, alkyl ring, or alkenyl ring, and wherein the straight or branched C$_1$-C$_{12}$ alkyl is optionally substituted with a hydroxy, halogen, —COOR$^6$ wherein R$^6$ is defined above, —CONR$^7$R$^8$ wherein R$^7$ and R$^8$ are defined above, cyclo(C$_3$-C$_6$ alkyl)methyl, —OR$^9$ wherein R$^9$ is C$_1$-C$_6$ alkyl, C$_1$-C$_6$ perhaloalkyl, phenyl, benzyl, or heterocyclic, —SR$^9$, —OR$^{10}$OR$^9$ wherein R$^{10}$ is C$_1$-C$_6$ alkylene, C$_1$-C$_6$ perhaloalkylene, phenyl, or heterocyclic and R$^9$ is as defined above, C$_1$-C$_6$ perhaloalkyl, —NR$^{11}$R$^{12}$ wherein R$^{11}$ and R$^{12}$ are independently hydrogen or C$_1$-C$_6$ alkyl, —NHC(O)R$^{13}$ wherein R$^{13}$ is hydrogen, C$_1$-C$_6$ alkyl, carboxyalkyl, or aminoalkyl, —NC(=NR$^{14}$)NR$^{15}$ wherein R$^{14}$ and R$^{15}$ are each independently hydrogen or C$_1$-C$_6$ alkyl, —N(R$^{16}$)OR$^{17}$ wherein R$^{16}$ and R$^{17}$ are each independently hydrogen or C$_1$-C$_6$ alkyl, —N(R$^{18}$)NR$^{19}$R$^{20}$ wherein R$^{18}$, R$^{19}$, and R$^{20}$ are each independently hydrogen or C$_1$-C$_6$ alkyl;
—C$_1$-C$_{12}$ perhaloalkyl;
—OR$^9$ wherein R$^9$ is as defined above;
—SR$^9$ wherein R$^9$ is as defined above;
—O—R$^{10}$OR$^9$ wherein R$^9$ and R$^{10}$ are as defined above;
—NR$^{11}$R$^{12}$ wherein R$^{11}$ and R$^{12}$ are as defined above;
—N(R$^{18}$)NR$^{19}$R$^{20}$ wherein R$^{18}$, R$^{19}$, and R$^{20}$ are as defined above; or
phenyl, —O(phenyl), —O(benzyl), heterocyclic, or —O(heterocyclic) group which may be unsubstituted, or mono-, di-, or trisubstituted with one or more of hydroxy, amino, —NHC(O)R$^{13}$ wherein R$^{13}$ is defined above, azido, nitro, cyano, halogen, sulfonamide, —COOR$^6$ wherein R$^6$ is defined above, —CONR$^7$R$^8$ wherein R$^7$ and R$^8$ are defined above, C$_1$-C$_6$ alkyl, C$_1$-C$_6$ perfluoroalkyl, —OR$^9$ wherein R$^9$ is as defined above, —SR$^9$, —NR$^{11}$R$^{12}$ wherein R$^{11}$ and R$^{12}$ are as defined above, or —N(R$^{18}$)NR$^{19}$R$^{20}$ wherein R$^{18}$, R$^{19}$, and R$^{20}$ are as defined above; and
wherein R$^1$ is
hydroxy;
amino;
azido;
nitro;
cyano;
halogen;
sulfonamide;
—COOR$^6$ wherein R$^6$ is hydrogen or C$_1$-C$_{12}$ alkyl;
—CONR$^7$R$^8$ wherein R$^7$ and R$^8$ are each independently hydrogen or C$_1$-C$_{12}$ alkyl;
—OR$^9$ wherein R$^9$ is as defined above;
—SR$^9$ wherein R$^9$ is as defined above;
—O—R$^{10}$OR$^9$ wherein R$^9$ and R$^{10}$ are as defined above;
—NR$^{11}$R$^{12}$ wherein R$^{11}$ and R$^{12}$ are as defined above;
—N(R$^{18}$)NR$^{19}$R$^{20}$ wherein R$^{18}$, R$^{19}$, and R$^{20}$ are as defined above; or
phenyl, —O(phenyl), —O(benzyl), heterocyclic, or —O(heterocyclic) group which may be unsubstituted, or mono-, di-, or trisubstituted with one or more of hydroxy, amino, —NHC(O)R$^{13}$ wherein R$^{13}$ is defined above, azido, nitro, cyano, halogen, sulfonamide, —COOR⁶ wherein R⁶ is defined above, —CONR⁷R⁸ wherein R⁷ and R⁸ are defined above, C₁-C₆ alkyl, C₁-C₆ perfluoroalkyl, —OR⁹ wherein R⁹ is as defined above, —SR⁹, —NR¹¹R¹² wherein R¹¹ and R¹² are as defined above, or —N(R¹⁸)NR¹⁹R²⁰ wherein R¹⁸, R¹⁹, and R²⁰ are as defined above;

wherein any two of R¹, R², R³, R⁴, and R⁵ may form a substituted or unsubstituted 5 to 7 member carbocyclic ring or a substituted or unsubstituted 5 to 7 member heterocyclic ring wherein the substitution is hydroxy, amino, nitro, halogen, sulfonamide, —COOR⁶, —CONR⁷R⁸, cyclo(C₃-C₆ alkyl)methyl, C₁-C₆ alkyl, C₁-C₆ perfluoroalkyl, —OR⁹, —SR⁹, —OR¹⁰OR⁹, —NR¹¹R¹², —NHC(O)R¹³, NC(=NR¹⁴)NR¹⁵, —N(R¹⁶)OR¹⁷, or —N(R¹⁸)NR¹⁹R²⁰ wherein R⁶ to R²⁰ are defined above; and with the proviso that at least one of R², R³, R⁴ and R⁵ is not hydrogen.

2. The compound of claim 1, wherein B is cytosine; thymine; uracil; 5-methylpyrimidin-1-yl-2,4(1H,3H)-dione; 5-ethylpyrimidin-1-yl-2,4(1H,3H)-dione; 5-chloropyrimidin-1-yl-2,4(1H,3H)-dione; 5-fluoropyrimidin-1-yl-2,4(1H,3H)-dione; 5-bromopyrimidin-1-yl-2,4(1H,3H)-dione; 5-iodopyrimidin-1-yl-2,4(1H,3H)-dione; 5-trifluoromethylpyrimidin-1-yl-2,4(1H,3H)-dione; 5-aminopyrimidin-1-yl-2,4(1H,3H)-dione; 5-(methylamino)pyrimidin-1-yl-2,4(1H,3H)-dione; 5-(dimethylamino)pyrimidin-1-yl-2,4(1H,3H)-dione; 5-hydroxypyrimidin-1-yl-2,4(1H,3H)-dione; 4-amino-pyrimidin-1-yl-2(1H)-one; 4-amino-5-chloropyrimidin-1-yl-2(1H)-one; 4-amino-5-bromopyrimidin-1-yl-2(1H)-one; 4-amino-5-fluoropyrimidin-1-yl-2(1H)-one; 4-amino-5-iodopyrimidin-1-yl-2(1H)-one; 4-amino-5-methylpyrimidin-1-yl-2(1H)-one; 3,4-dihydro-5-methyl-4-(methylamino)pyrimidin-1-yl-2(1H)-one; 3,4-dihydro-5-chloro-4-(methylamino)pyrimidin-1-yl-2(1H)-one; 3,4-dihydro-5-fluoro-4-(methylamino)pyrimidin-1-yl-2(1H)-one; or 3,4-dihydro-5-methyl-4-(hydroxyamino)pyrimidin-1-yl-2(1H)-one.

3. The compound of claim 1, wherein R¹ is hydroxy, azido, chloro, bromo, or fluoro.

4. The compound of claim 1, wherein R² or R⁴ is hydrogen, azido, chloro, bromo, or fluoro.

5. The compound of claim 1, wherein R³ or R⁵ is hydroxymethyl, azido, chloro, bromo, or fluoro.

6. The compound of claim 1, wherein when either R² or R⁴ and either R³ or R⁵ are C, alkyl substituted with a hydroxy or —O-benzyl group, and the other R² or R⁴ and R³ or R⁵ are hydrogen, then B is not 4-aminopyrimidin-1-yl-2-one or 4-amino-5-fluoro-pyrimidin-1-yl-2-one.

7. The compound of claim 1, wherein the oxetane comprises the Formula 1a:

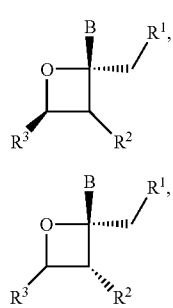

(1a)

(1b)

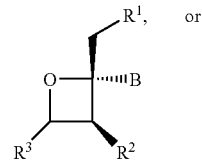

(1c)

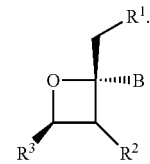

(1d)

8. A pharmaceutical composition, comprising a pharmaceutically acceptable amount of the compound of claim 1 and a pharmaceutically acceptable carrier.

9. A compound, comprising:
an oxetane of Formula 1,

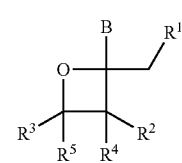

(1)

a pharmaceutically acceptable salt, diastereomer, or mixture thereof wherein:
B is a pyrimidin-1-yl or a heterocyclic isostere of a pyrimidin-1-yl, wherein the pyrimidin-1-yl or heterocyclic isostere of a pyrimidin-1-yl comprises

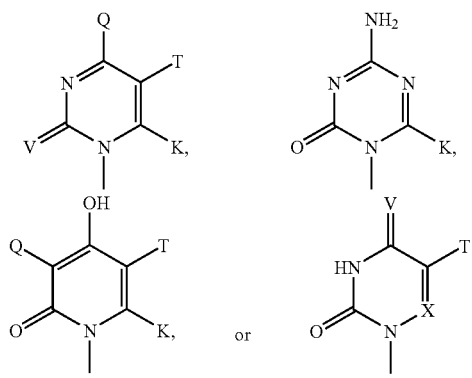

wherein
V is O or S;
X is C or N;
Q, T, or K are each independently
hydrogen;
hydroxy;
halogen;
cyano;
azido;
nitro;
hydroxyamino;
—COOR³⁶ wherein R³⁶ is hydrogen or C₁-C₁₂ alkyl;

—CONR³⁷R³⁸ wherein R³⁷ and R³⁸ are each independently hydrogen or $C_1$-$C_{12}$ alkyl;

—OR³⁹ wherein R³⁹ is $C_1$-$C_6$ alkyl, $C_1$-$C_6$ perhaloalkyl, phenyl, benzyl, or heterocyclic;

—SR³⁹ wherein R³⁹ is hydrogen, $C_1$-$C_6$ alkyl, $C_1$-$C_6$ perhaloalkyl, phenyl, benzyl, or heterocyclic;

phenyl, —O(phenyl), benzyl, —O(benzyl), heterocyclic or —O(heterocyclic) group which may be unsubstituted, or mono-, di- or trisubstituted with one or more of hydroxy, amino, azido, nitro, cyano, halogen, sulfonamide, carboxyl, $C_1$-$C_6$ alkyl, $C_1$-$C_6$ perfluoroalkyl, —OR³⁹, —SR³⁹ wherein R³⁹ is as defined above, —NR⁴⁰R⁴¹ wherein R⁴⁰ and R⁴¹ are independently hydrogen or $C_1$-$C_{12}$ alkyl, —N(R⁴²)NR⁴³R⁴⁴ wherein R⁴², R⁴³, and R⁴⁴ are each independently hydrogen or $C_1$-$C_{12}$ alkyl;

—NR⁴⁰R⁴¹ wherein R⁴⁰ and R⁴¹ are as defined above;

—NHC(O)R⁴² wherein R⁴² is hydrogen, $C_1$-$C_{12}$ alkyl, carboxyalkyl, or aminoalkyl;

straight or branched $C_1$-$C_{12}$ alkyl which is optionally substituted with a hydroxy or halogen and in which the branched alkyl chains may form a 3 to 7 member heteroalkyl, alkyl ring, or alkenyl ring;

$C_1$-$C_{12}$ alkenyl;

$C_1$-$C_2$ alkenyl;

—CH₂NR⁴³R⁴⁴ wherein R⁴³ and R⁴⁴ are independently hydrogen or $C_1$-$C_{12}$ alkyl; or

wherein m is 1-5; and wherein R², R³, R⁴, and R⁵ are each independently hydrogen; or straight or branched $C_1$-$C_{12}$ alkyl optionally substituted with a hydroxy or —OR⁹ wherein R⁹ is $C_1$-$C_6$ alkyl, $C_1$-$C_6$ perhaloalkyl, phenyl, benzyl, or heterocyclic; and wherein R¹ is hydroxy, azido, or halogen; and with the proviso that at least one of R², R³, R⁴ and R⁵ is not hydrogen.

10. The compound of claim 9, wherein B is cytosine; thymine; uracil; 5-methylpyrimidin-1-yl-2,4(1H,3H)-dione; 5-ethylpyrimidin-1-yl-2,4(1H,3H)-dione; 5-chloropyrimidin-1-yl-2,4(1H,3H)-dione; 5-fluoropyrimidin-1-yl-2,4(1H, 3H)-dione; 5-bromopyrimidin-1-yl-2,4(1H,3H)-dione; 5-iodopyrimidin-1-yl-2,4(1H,3H)-dione; 5-trifluoromethylpyrimidin-1-yl-2,4(1H,3H)-dione; 5-aminopyrimidin-1-yl-2,4(1H,3H)-dione; 5-(methylamino)pyrimidin-1-yl-2,4(1H,3H)-dione; 5-(dimethylamino)pyrimidin-1-yl-2,4(1H,3H)-dione; 5-hydroxypyrimidin-1-yl-2,4 (1H,3H)-dione; 4-amino-pyrimidin-1-yl-2(1H)-one; 4-amino-5-chloropyrimidin-1-yl-2(1H)-one; 4-amino-5-bromopyrimidin-1-yl-2(1H)-one; 4-amino-5-fluoropyrimidin-1-yl-2(1H)-one; 4-amino-5-iodopyrimidin-1-yl-2(1H)-one; 4-amino-5-methylpyrimidin-1-yl-2(1H)-one; 3,4-dihydro-5-methyl-4-(methylamino)pyrimidin-1-yl-2(1H)-one; 3,4-dihydro-5-chloro-4-(methylamino)pyrimidin-1-yl-2(1H)-one; 3,4-dihydro-5-fluoro-4-(methylamino)pyrimidin-1-yl-2(1H)-one; or 3,4-dihydro-5-methyl-4-(hydroxyamino)pyrimidin-1-yl-2(1H)-one.

11. The compound of claim 9, wherein when either R² or R⁴ and either R³ or R⁵ are $C_1$ alkyl substituted with a hydroxy or —O-benzyl group, and the other R² or R⁴ and R³ or R⁵ are hydrogen, then B is not 4-aminopyrimidin-1-yl-2-one or 4-amino-5-fluoro-pyrimidin-1-yl-2-one.

12. The compound of claim 9, wherein the oxetane comprises the Formula:

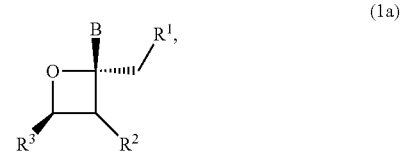

(1a)

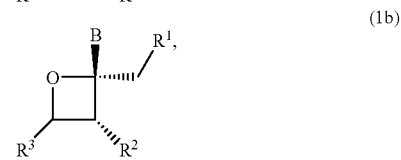

(1b)

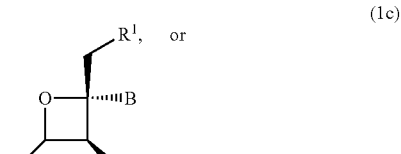

(1c)

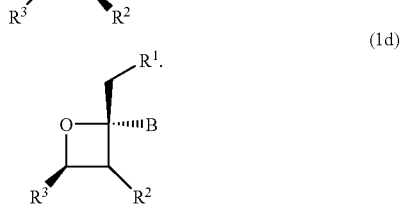

(1d)

* * * * *